US009169462B2

(12) United States Patent
Refaeli et al.

(10) Patent No.: US 9,169,462 B2
(45) Date of Patent: Oct. 27, 2015

(54) METHODS FOR PREPARING MATURE ERYTHROCYTES FROM CONDITIONALLY IMMORTALIZED HEMATOPOIETIC STEM CELLS

(75) Inventors: Yosef Refaeli, Denver, CO (US); Brian Curtis Turner, Denver, CO (US)

(73) Assignee: Taiga Biotechnologies, Inc., Aurora, CO (US)

( * ) Notice: Subject to any disclaimer, the term of this patent is extended or adjusted under 35 U.S.C. 154(b) by 753 days.

(21) Appl. No.: 12/506,894

(22) Filed: Jul. 21, 2009

(65) Prior Publication Data

US 2010/0047217 A1    Feb. 25, 2010

Related U.S. Application Data

(60) Provisional application No. 61/082,410, filed on Jul. 21, 2008.

(51) Int. Cl.
*A61K 35/12* (2015.01)
*C12N 5/00* (2006.01)
*A61P 43/00* (2006.01)
*C12N 5/078* (2010.01)

(52) U.S. Cl.
CPC .......... *C12N 5/0641* (2013.01); *C12N 2510/04* (2013.01); *C12N 2799/027* (2013.01); *C12N 2800/30* (2013.01); *C12N 2840/203* (2013.01)

(58) Field of Classification Search
CPC ........... C12N 2840/203; C12N 5/0641; C12N 2510/04; C12N 2800/30; C12N 2799/027
See application file for complete search history.

(56) References Cited

U.S. PATENT DOCUMENTS

| | | | |
|---|---|---|---|
| 4,963,489 A | 10/1990 | Naughton et al. | |
| 5,476,996 A | 12/1995 | Wilson et al. | |
| 5,698,767 A | 12/1997 | Wilson et al. | |
| 5,811,301 A | 9/1998 | Cameron | |
| 5,824,837 A | 10/1998 | Chen et al. | |
| 5,849,288 A | 12/1998 | Reisner | |
| 6,451,558 B1 | 9/2002 | Cooke et al. | |
| 7,135,287 B1 | 11/2006 | Lonberg et al. | |
| 7,311,920 B1 | 12/2007 | Devico et al. | |
| 7,582,745 B2 | 9/2009 | Sah et al. | |
| 7,767,453 B2 | 8/2010 | Zhang | |
| 2001/0049393 A1 | 12/2001 | Coller et al. | |
| 2002/0098166 A1 | 7/2002 | Havemann et al. | |
| 2003/0072794 A1 | 4/2003 | Boulikas | |
| 2003/0138859 A1 | 7/2003 | Barbera-Guillem et al. | |
| 2003/0220286 A1* | 11/2003 | Abruzzese et al. ............ 514/44 |
| 2005/0220705 A1 | 10/2005 | Brooks et al. | |
| 2005/0281816 A1 | 12/2005 | Lamping et al. | |
| 2006/0115898 A1 | 6/2006 | Zhang et al. | |
| 2006/0154331 A1 | 7/2006 | Avidan et al. | |
| 2006/0156422 A1 | 7/2006 | Dalrymple et al. | |
| 2007/0011753 A1 | 1/2007 | Ito et al. | |
| 2007/0067854 A1 | 3/2007 | Habu et al. | |
| 2007/0093420 A1 | 4/2007 | Yeomans et al. | |
| 2007/0116691 A1 | 5/2007 | Cambier | |
| 2007/0130628 A1 | 6/2007 | Brown | |
| 2007/0248618 A1 | 10/2007 | Cohen | |
| 2009/0291094 A1 | 11/2009 | Refaeli | |
| 2010/0047217 A1 | 2/2010 | Refaeli | |
| 2010/0055129 A1 | 3/2010 | Refaeli | |
| 2010/0233804 A1 | 9/2010 | Zhou et al. | |
| 2010/0279351 A1 | 11/2010 | Refaeli et al. | |
| 2010/0297763 A1 | 11/2010 | Cambier et al. | |
| 2011/0218210 A1 | 9/2011 | Refaeli et al. | |

FOREIGN PATENT DOCUMENTS

| | | |
|---|---|---|
| EP | 1 103 615 | 5/2001 |
| EP | 1103615 A1 | 5/2001 |
| EP | 1357184 A2 | 10/2003 |
| EP | 1792627 A1 | 6/2007 |
| GB | 2387599 | 10/2003 |
| JP | 2001-518300 | 10/2001 |
| JP | 2003-514565 | 4/2003 |
| JP | 2005-525085 | 8/2005 |
| JP | 2005523012 A | 8/2005 |
| JP | 2005-527211 A | 9/2005 |
| JP | 2009511081 A | 3/2009 |
| WO | 94/04686 A1 | 3/1994 |
| WO | 94/19465 A2 | 9/1994 |
| WO | WO-98-10058 | 3/1998 |
| WO | WO-98/10058 | 3/1998 |
| WO | WO-99/16884 | 4/1999 |
| WO | 99/45962 A1 | 9/1999 |
| WO | WO-99/53023 | 10/1999 |
| WO | WO-99-53028 | 10/1999 |
| WO | WO-00/09669 | 2/2000 |
| WO | WO-00-09669 | 2/2000 |
| WO | 00/62067 A1 | 10/2000 |
| WO | WO-01-38548 A2 | 5/2001 |
| WO | WO-02/057436 | 7/2002 |
| WO | WO-03/038057 | 5/2003 |
| WO | 03/089580 A2 | 10/2003 |
| WO | WO-03/089580 | 10/2003 |
| WO | WO-03-089630 A2 | 10/2003 |
| WO | WO-03/097675 | 11/2003 |
| WO | WO 2005/014785 * | 2/2005 |
| WO | 2005/084158 A2 | 9/2005 |
| WO | WO-2006-032876 | 3/2006 |
| WO | 2006/116512 A1 | 11/2006 |
| WO | 2007/047583 A2 | 4/2007 |
| WO | 2007/067183 A1 | 6/2007 |
| WO | WO-2008/112922 | 9/2008 |
| WO | WO-2009/059304 | 5/2009 |
| WO | 2009/139930 A2 | 11/2009 |
| WO | WO-2010/011644 | 1/2010 |
| WO | WO-2010/025421 | 3/2010 |

OTHER PUBLICATIONS

Miharada et al., Nature Biotechnology, 24(10): 1255-1256, 2006.*

(Continued)

*Primary Examiner* — Thaian N Ton

(74) *Attorney, Agent, or Firm* — Foley & Lardner LLP

(57) ABSTRACT

Provided herein are methods for preparing differentiated cells, and the cells prepared by such methods.

15 Claims, 8 Drawing Sheets

(56) References Cited

OTHER PUBLICATIONS

Office Action received for Australian Patent Application No. 2009285547, mailed on Jul. 25, 2011, 2 pages.
Office Action received for European Patent Application No. 08743862.8, mailed on Sep. 23, 2010, 6 pages.
Extended European Search Report received for European Patent Application No. 09810692.5, mailed on Jul. 11, 2011, 5 pages.
Office Action received for Israel Patent Application No. 208810, mailed on Nov. 2, 2011, 3 pages of English Translation only.
Office Action received for Israel Patent Application No. 209343, mailed on Nov. 2, 2011, 3 pages of English Translation only.
Office Action received for Israel Patent Application No. 209968, mailed on Nov. 2, 2011, 3 pages of English Translation only.
Office Action received for Korean Patent Application No. 10-2009-7021320, mailed on Jul. 29, 2011, 7 pages (3 pages of English Translation and 4 pages of Office Action).
International Search Report and Written Opinion received for PCT Patent Application No. PCT/US2008/082263, mailed on Jun. 25, 2009, 8 pages.
International Search Report and Written Opinion received for PCT Patent Application No. PCT/US2009/003105, mailed on Jan. 15, 2010, 9 pages.
International Preliminary Report on Patentability received for PCT Patent Application No. PCT/US2008/082263, issued on May 4, 2010, 6 pages.
International Search Report and Written Opinion received for PCT Patent Application No. PCT/US2009/055443, mailed on Jun. 30, 2010, 11 pages.
International Preliminary Report on Patentability Received for Application No. PCT/US2009/003105, mailed on Nov. 17, 2010, 6 pages.
International Preliminary Report on Patentability received for PCT Patent Application No. PCT/US2009/055443, issued on Mar. 10, 2011, 7 pages.
Non Final Office Action received for U.S. Appl. No. 12/962,197, mailed on Aug. 26, 2011, 20 pages.
Non Final Office Action received for U.S. Appl. No. 12/048,148, mailed on Oct. 13, 2011, 20 pages.
Non-Final Office Action received for U.S. Appl. No. 12/550,166, mailed on Jan. 11, 2012, 24 pages.
Berkson et al., "Pilot Screening Programme for Small Molecule Activators of p53", International Journal of Cancer, vol. 115, 2005, pp. 701-710.
Caron et al., "Endosome disruption enhances the functional nuclear delivery of Tat-fusion proteins", Biochemical and Biophysical Research Communications, vol. 319, 2004, pp. 12-20.
Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845.
Coller et al., "Expression Analysis with Oligonucleotide Microarrays Reveals that MYC Regulates Genes Involved in Growth, Cell Cycle, Signaling, and Adhesion", Proc. Natl. Acad. Sci. USA, vol. 97, No. 7, Mar. 28, 2000, pp. 3260-3265.
Dang et al., "Identification of the Human c-myc Protein Nuclear Translocation Signal", Molecular and Cellular Biology, vol. 8, No. 10, Oct. 1988, pp. 4048-4054.
Habib et al., "Myc Stimulates B Lymphocyte Differentiation and Amplifies Calcium Signaling", J.Cell Biol., vol. 179, No. 4, 2007, pp. 717-731.
Hiramatsu et al., "Complete Reconstitution of Human Lymphocytes from Cord Blood CD34+ Cells Using the NOD/ SCID/ycnull Mice Model", Blood, vol. 102, No. 3, Aug. 1, 2003, pp. 873-880.
Huang et al., "Dynamic Regulation of C-Myc Proto-Oncogene Expression during Lymphocyte Development Revealed by a GFP-C-Myc Knock-In Mouse", Eur. J. Immunol., vol. 38, No. 2, 2008, pp. 342-349.

Littlewood et al., "A Modified Oestrogen Receptor Ligand-Binding Domain as an Improved Switch for the Regulation of Heterologous Proteins", Nucleic Acids Research, vol. 23, No. 10, May 25, 1995, pp. 1686-1690.
Qin et al., "Nuclear Factor κB Nuclear Translocation Upregulates c-Myc and p53 Expression during NMDA ReceptorMediated Apoptosis in Rat Striatum", The Journal of Neuroscience, vol. 19, No. 10, May 15, 1999, pp. 4023-4033.
Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270.
Refaeli, Y, "The B-Cell Antigen Receptor and Overexpression of MYC Can Cooperate in the Genesis of B-Cell Lymphomas", PLOS Biology, vol. 6, No. 6, e152, Jun. 2008, pp. 1208-1225.
Young et al., "B-Cell Receptor Signaling in the Genesis and Maintenance of B-Cell Lymphoma", Future Oncology, vol. 4, No. 5, 2008, pp. 591-594.
International Preliminary Report on Patentability received for PCT Patent Application No. PCT/US2006/040379, mailed on Apr. 23, 2008, 5 pages.
PCT/US09/51242 Search Report dated Feb. 19, 2010.
Refaeli, Y. et al., "The protooncogene MYC can break B cell tolerance," PNAS 102(11):4097-4102 (2005).
PCT/US09/51242 IPER mailed Feb. 3, 2011.
U.S. Appl. No. 12/467,957 Office Action mailed Feb. 28, 2011.
U.S. Appl. No. 12/467,957 Office Action mailed Oct. 13, 2010.
U.S. Appl. No. 12/048,148 Office Action mailed Jan. 19, 2011.
U.S. Appl. No. 11/583,970 Office Action mailed Nov. 4, 2009.
U.S. Appl. No. 11/583,970 Office Action mailed Mar. 23, 2009.
U.S. Appl. No. 11/583,970 Office Action mailed Nov. 26, 2008.
U.S. Appl. No. 11/583,970 Office Action mailed Mar. 12, 2008.
EP 08743862 Supplementary Search Report dated Feb. 9, 2010.
PCT/US08/56896 Written Opinion dated Jul. 18, 2008.
PCT/US08/56896 Internationl Preliminary Report on Patentability dated Sep. 15, 2009.
EP08743862 Office Action dated May 14, 2010.
Extended European Search Report received for European Patent Application No. 09800871.7, mailed on Jun. 24, 2011, 5 pages.
Carotta et al., "Directed differentiation and mass cultivation of pure erythroid progenitors from mouse embryonic stem cells", Blood, vol. 104, No. 6, Sep. 15, 2004, pp. 1873-1880.
Kelso et al., "Survival of the Myeloid Progenitor Cell Line FDC-P1 is Prolonged by Interferon-gamma or Interleukin-4", Growth Factors, vol. 6, 1992, pp. 233-242.
Office Action received for Israel Patent Application No. 200919, mailed on Dec. 5, 2011, 2 pages of English Translation only.
Office Action received for Chinese Patent Application No. 200980126312.4, mailed on Jan. 30, 2012, 14 pages ( 7 pages of English translation and 7 pages of Office Action).
Bunting et al., "Restoration of lymphocyte function in Janus kinase 3-deficient mice by retroviral-mediated gene transfer," Nature Medicine 4:58-64 (1998).
Chadwick et al., "Notch Signaling Induces Apoptosis in Primary Human CD34+ Hematopoietic Progenitor Cells," Stem Cells 24:203-210 (2007).
Cheng et al., "BCL-2, BCL-XL Sequester BH3 Domain-Only Molecules Preventing BAX- and BAK-Mediated Mitochondrial Apoptosis," Molecular Cell 8:705-711 (2001).
Conti, L. et al., "Gene therapy using neural stem cells," Methods Mol. Biol. 198:233-244 (2002).
DeoCampo et al., "Cooperation of bcl-2 and myc in the neoplastic transformation of normal rat lever epithelial cells is related to the down-regulation of gap junction-mediated intercellular communication," Carcinogenesis 21(8):1501-1506 (2000).
Eilers, M. et al., "Chimeras of MYC Oncoprotein and Steroid Receptors Cause Hormone-Dependent Transformation of Cells," Nature 340(6228):66-68 (1989).
Eischen et al., "Apoptosis Triggered by Myc-Induced Suppression of Bcl-XL or Bcl-2 Is Bypassed during Lymphomagenesis," Molecular Cell Biology 21:5063-5070 (2001).
EP 06826025 Supplementary Search Report dated Jul. 28, 2009.

(56) References Cited

OTHER PUBLICATIONS

Esdar, C. et al., "Differentiation-associated apoptosis of neural stem cells is effected by Bcl-2 overexpression: impact on cell lineage determination," Eur. J. Cell Biol. 80(8):539-553 (2001).
Felsher and Bishop, "Reversible Tumorigenesis by MYC in Hematopoietic Lineages," Molecular Cell 4:199-207 (1999).
Gauss, "DEAE-dextran enhances electoportation of mammalian cells," Nucleic Acids Research 20(24):6739-6740 (1992).
Guzman et al., "Preferential induction of apoptosis for primary human leukemic stem cells," PNAS 99(25):16220-16225 (2002).
Hoffman, "Progress in the develoment of systems for in vitro expansion of human hematopoietic stem cells," Curr. Op. Hematology 6(3):14 pages (1999).
Horton, S.J. et al., "Continuous MLL-ENL expression is necessary to establish a "Hox Code" and maintain immortalization of hematopoietic progenitor cells," Cancer Res. 65(20):9245-9252 (2005).
Hoshimaru, M. et al., "Differentiation of the immortalized adult neuronal progenitor cell line HC2S2 into neurones by regulatable suppression of the V-MYC oncogene," Proceedings of the National Acadamy of Sciences of USA 93(4):1518-1523 (1996).
Howard, M.J. et al., "Transplantation of apoptosis-resistant embryonic stem cells into the injured rat spinal cord," Somatosensory & Motor Research 22(1-2):37-44 (2005).
IPER PCT/US06/40370, Apr. 23, 2008.
Korbling et al., "Allogenic Blood Stem Cell Transplantation: Peripheralization and Yield of Donor-Derived Primitive Hematopoietic Progenitor Cells (CD34+Thy-1dim) and Lymphoid Subsets, and Possible Predictors of Engraftment and Graft-Versus-Host Disease," Blood 86:2842-2848 (1995).
Krosl et al., "In vitro expansion of hematopoietic stem cells by recombinandt TAT-HOXB4 protein," Nature Mediciine 9(11):1428-1432 (2003).
MacPherson, P. et al., "Activity-dependent gene regulation in conditionally-immortalized muscle precursor cell lines," J. Cell. Biol. 91(4):821-839 (2004).
McCarthy, "Underground movement," Nature Reviews Cancer 7, p. 1 (2007) published online Oct. 11, 2007.
Melkonyan et al., "Electroporation efficiency in mammlian cells is increased by dimethyl sulfoxide (DMSO)," Nucleic Acids Research 24:4356-4357 (1996).
Miller et al., "Expansion in vitro of adult murine hematopoietic stem cells with transplantable lympho-myeloid reconsituting ability," PNAS USA 94:13648-13653 (1997).
Moore et al., "In Vitro Maintenance of Highly Purified, Transplantable hematopoietic Stem Cells," Blood 89(12):4337-4347 (1997).
Mooslehner et al., Retroviral Integration Sites in Transgenic Mov Mice Frequently Map in the Vicinity of Transcribed DNA Regions,: J. Virology 64:3056-3058 (1990).
PCT/US06/40379 Search Report and Written Opinion mailed Sep. 24, 2007.
PCT/US08/56896 Search Report dated Aug. 14, 2008.
Pierelli et al., "Modulation of bcl-2 and p27 in human primitive proliferating hematopoietic progenitors by autocrine TGF-B1 is a cell cycle-independent effect and influences their hematopoietic potential,"Blood 95:3001-3010 (2000).
Pinto et al., "Hematopoietic progenitor/stem cells immortalized by Lhx2 generate functional hematopoietic cells in vivo," Blood 99(11):3939-3946 (2002).
Podsypanina, K. et al., "Oncogene cooperation in tumor maintenance and tumor recurrence in mouse mammary tumors induced by MYC and mutant Kras," PNAS 105(13):5242-5247 (2008).
Pollock, K. et al., "A conditionally immortal clonal stem cell line from human cortical neuroepithelium for the treatment of ischemic stroke," Exp. Neurology 199(1):143-155 (2006).
Raymon, H.K. et al., "Immortalized human dorsal root ganglion cells differentiate into neurons with nociceptive properties," J. Neuroscience 19(13):5420-5428 (1999).
Refaeli, Y. et al., "The protooncogene MYC can break B cell tolerance," PNAS 102(11):4097-4102 (2005.
Richter et al., "Lhx2 expression in hematopoietic progenitor/stem cells in vivo causes a chronic myeloproliferative disorder and altered globin expression," J. Hematology 88(12):1336-1347 (2003).
Roh, M. et al., "Transgenic Mice for Cre-Inducible Overexpression of the Oncogenes c-MYC and Pim-1 in Multiple Tissues," Genesis 44:447-453 (2006).
Rosenwald et al., "Increased expression of eukaryotic translation initiation facots e1F-4E and e1F-2alpha in response to growth induction by c-myc," PNAS USA 90:6175-6178 (1993).
Sauer, "Inducible Gene Targeting in Mice Using the Cre/1ox System," Methods 14:381-392 (1998).
Schmidt, E.V. et al., "Transgenic mice bearing the human c-myc gene activated by an immunoglobulin enhancer: A pre-B-cell lymphoma model," PNAS USA 85:60476051 (1988).
Schroy and Todd, "A Simple Method for Freezing and Thawing Cultured Cells," Methods in Cell Science 2:309-310 (1976).
Schwarze et al., "Protein transduction: unrestricted delivery into all cells?"Trends Cell Biol. 10:290-295 (2000).
Sipone, S. et al., "Modeling brain pathologies using neural stem cells," Methods Mol. Biol. 198:245-262 (2002).
Takahashi et al., "Induction of Pluripotent Stem Cells from Mouse Embryonic and Adult Fibroblast Cultures by Defined Factors," Cell 126:663-676 (2006).
Tsai et al., "Lymphohematopoietic progenitors immortalized by a retroviral vetor harboring a dominant-negative retinoic acid receptor can recapitulate lymphoid, myeloid, and erythroid development," Genes & Dev. 8:2831-2841 (1994).
Vaux et al., "Bcl-2 gene promotes haemopoietic cell survival and cooperates with c-myc to immortalize pre-B cells," Nature 334:440-442 (1988).
Varnum-Finney et al., "Pluripotent, cytokine-dependent, hematopoietic stem cells are immortalized by constitutive Notch1 signaling," Nature Medicine 6(11)1278-1281 (2000).
Wang et al., "Primitive Human Hematopoietic Cells Are Enriched in Cord Blood Compared with Adult Bone Marrow or Mobilized Peripheral Blood as Measured by the Quantitative In Vivo SCID-Repopulating Cell Assay," Blood 89:3919-3924 (1997).
Wikipedia [online], 2008, [retrieved on Nov. 13, 2008]. Retrieved from the Internet: <URL: http//en.wikipedia.org/wiki/Stem_cell>, pp. 1-11.
Wilson et al., "c-Myc controls the balance between hematopoietic stem cell self-renewal and differentiation," Genes and Development 18:2474-2763 (2007).
Wurm and Bernard, "Large-scale transient expression of mammalian cells for recombinant protein production," Curr. Op. Biotech. 10:156-159 (1999).
Yanai et al., "A novel stroma cell-dependent hematopoietic cell line established from temperature-sensitive SV40 T-antigen transgenic mice," Exp. Hematology 27:1087-1096 (1999).
U.S. Appl. No. 12/048,148 filed Mar. 13, 2008.
U.S. Appl. No. 12/550,166 filed Aug. 28, 2009.
Final Office Action received for Korean Patent Application No. 10-2009-7021320, mailed on May 29, 2013, 6 pages (3 pages of English Translation and 3 pages of Office Action).
Office Action received for Chinese Patent Application No. 200880015602.7, mailed on May 9, 2013, 13 pages (8 pages of English Translation and 5 pages of Official copy).
Choi, et al., "Status Epilepticus-Induced Somatostatinergic Hilar Interneuron Degeneration Is Regulated by Striatal Enriched Protein Tyrosine Phosphatase", Journal of Neuroscience, (2007), vol. 27, No. 11, pp. 2999-3009.
English Translation of Office Action received for Chinese Patent Application No. 200980126312.4 (106417-0122) dated Jan. 22, 2014, 3 pages.
English Translation of Office Action received for Japanese Patent Application No. 2011-525258 (106417-0113) dated Feb. 17, 2014, 4 pages.
Ho, et al., "Synthetic Protein Transduction Domains: Enhanced Transduction Potential in Vitro and in Vivo", Cancer Research, (2001), vol. 61, pp. 474-477.
Iritani, et al., "c-Myc enhances protein synthesis and cell size during B lymphocyte development", PNAS, (1999), vol. 96, No. 23, pp. 13180-13185.

(56) References Cited

OTHER PUBLICATIONS

Jadlowsky, et al., "Dominant negative mutant Cyclin T1 proteins inhibit HIV transcription by specifically degrading Tat", Retrovirology, (2008), vol. 5, Article 63, 12 pages.
Kashio, et al., "A Protein Derived From the Fusion of TAT Peptide and FNK, a Bcl-xL Derivative, Prevents Cochlear Hair Cell Death From Aminoglycoside Ototoxicity in Vivo", Journal of Neuroscience Research, (2007), vol. 85, No. 7, pp. 1403-1412.
Kitada, et al., "Reversal of Chemoresistance of Lymphoma Cells by Antisense-Mediated Reduction of bcl-2 Gene Expression", Antisense Research and Development, (1994), vol. 4, pp. 71-79.
Non-final Office Action on U.S. Appl. No. 12/467,957 (106576-0103) dated Apr. 4, 2014, 14 pages.
Non-final Office Action on U.S. Appl. No. 13/795,659 (106417-0136) dated Mar. 10, 2014, 11 pages.
Non-final Office Action on U.S. Appl. No. 13/797,648 (106417-0174) dated Apr. 3, 2014, 13 pages.
Office Action received for Australian Patent Application No. 2009246876 (106576-0106) dated Jan. 17, 2014, 6 pages.
Office Action received for European Application No. 09810692.5 (106417-0110) dated Feb. 25, 2014, 3 pages.
Office Action received for Indian Application No. 3332/DELNP/2008 (106417-0150) dated Aug. 23, 2013, 3 pages.
Rabbitts, et al., "Metabolism of c-myc gene products: c-myc mRNA and protein expression in the cell cycle", EMBO Journal, (1985), vol. 4, No. 8, pp. 2009-2015.
Snyder, et al., "Regulation of NMDA receptor trafficking by amyloid-3B2", Nature Neuroscience, (2005), vol. 8, No. 8, pp. 1051-1058.
Theis, et al., "Expression of the myc/His-Tagged Human Peptide Transporter hPEPT1 in Yeast for Protein Purification and Functional Analysis", Protein Expression and Purification, (2001), vol. 22, pp. 436-442.
Vaux, et al., "Immunologic competence of B cells subjected to constitutive c-myc oncogene expression in immunoglobulin heavy chain enhancer myc transgenic mice", J. Immunol., (1987), vol. 139, No. 11, pp. 3854-3860.
Office Action received for Chinese Patent Application No. 200880015602.7, mailed on Jan. 31, 2012, 16 pages (10 pages of English translation and 6 pages of Office Action).
Office Action received for European Patent Application No. 09810692.5, mailed on Mar. 28, 2012, 3 pages.
Final Office Action Received for U.S. Appl. No. 12/550,166, mailed on May 11, 2012, 12 pages.
Non Final Office Action Received for U.S. Appl. No. 12/048,148, mailed on May 11, 2012, 22 pages.
Oral Proceeding received for European Patent Application No. 08743862.8, mailed on May 14, 2012, 6 pages.
Deocampo, et al., "Cooperation of BCL-2 and MYC in the Neoplastic Transformation of Normal Rat Lever Epithelial Cells is Related to the Down-Regulation of Gap Junction-Mediated Intercellular Communication", Carcinogenesis, vol. 21, No. 8, pp. 1501-1506,(2000).
English Translation of Office Action on Chinese Application No. 200980127166.7 (106417-0109) dated Apr. 11, 2014, 3 pages.
English Translation of Office Action on Japanese Patent Application. No. 2012-221023 dated Apr. 22, 2014, 3 pages.
English Translation of Third Office Action on Japanese Patent Application No. 2009-553785 (1065760128) dated Apr. 22, 2014, 3 pages.
Examination Report for Indian Patent Application No. 3332/DELNP/2008 (106417-0150) dated Aug. 23, 2013, 6 pages.
Examination Report on Australian Patent Application No. 2012216462 (106417-0104) dated Mar. 6, 2014, 3 pages.
Final Office Action on U.S. Appl. No. 11/583,970 (106417-0140) dated Apr. 9, 2014, 20 pages.
Gauss et al., "DEAE-Dextran Enhances Electroportation of Mammalian Cells", Nucleic Acids Research, vol. 20, No. 4, pp. 6739-6740 (1992).
Non-final Office Action on U.S. Appl. No. 12/701383 (106417-0141) dated Jun. 13, 2014, 26 pages.
Notice of Allowance on U.S. Appl. No. 12/550,166 (106417-0103) dated Apr. 28, 2014, 4 pages.
Notification prior to Allowance of Israeli Patent Application No. 209343 (106417-0125) dated Apr. 7, 2014, 2 pages.
Office Action on Canadian Application No. 2,626,525 (106417-0143) dated Apr. 8, 2014, 4 pages.
Office Action on Canadian Patent Application No. 2,680,613 (106576-0121) dated Nov. 21, 2013, 3 pages.
Rosenwald, et al., "Increased Expression of Eukaryotic Translation Inhibition Factors eIF-4E and eIF-2alpha in Response to Growth Induction by C-MYC", Proc. Natl. Acad. Sci. USA, vol. 90, pp. 6175-6178, (1993).
Wilson, et al. "c-MYC Controls the Balance Between Hematopoietic Stem Cell Self-Renewal and Differentiation" Genes and Development, vol. 18, pp. 2747-2763 (2007).
Office Action received for Chinese Patent Application No. 200980126312.4, issued on Aug. 28, 2012, 12 pages (6 pages of English Translation and 6 pages of Office Action).
Office Action received for Korean Patent Application No. 10-2009-7021320, mailed on Sep. 18, 2012, 11 pages (7 pages of English Translation and 4 pages of Office Action).
Office Action received for Israel Patent Application No. 209343, mailed on Aug. 14, 2012, 4 pages.
English Translation of Fourth Office Action received for Chinese Patent Application No. 200880015602.7 (106576-0122) dated Nov. 11, 2013, 6 pages.
English Translation of Office Action received for Eurasian Patent Application No. 201001762/28 (106576-0108), posted Oct. 16, 2013, 1 page.
English translation of Office Action received for Israeli Patent Application No. 190946 (106417-0147), dated Apr. 22, 2013, 1 page.
English Translation of Office Action received for Israeli Patent Application No. 209968 (106417-0112) dated Jan. 2, 2014, 2 pages.
English translation of Office Action received for Japanese Application No. 2008-536713 (106417-0149) dated Aug. 5, 2013, 2 pages.
English Translation of Office Action received for Korean Patent Application No. 10-2008-7011791 (106417-0152) dated Jan. 15, 2014, 3 pages.
English Translation of Office Action received for Korean Patent Application No. 10-2013-7028338 (106417-0162), dated Jan. 15, 2014, 3 pages.
English Translation of Second Office Action received for Chinese Patent Application No. 200980127166.7 (106417-0109), dated Jun. 10, 2013, 1 page.
Extended European Search Report received for European Patent Application No. 06826025.6 (1064170145), mailed on Aug. 13, 2009, 8 pages.
Non-Final Office Action on U.S. Appl. No. 11/583,970 (106417-0140) dated Sep. 20, 2013, 19 pages.
Notice of Allowance received for U.S. Appl. No. 12/550,166, (106417-0103) mailed on Nov. 26, 2012, 9 pages.
Office Action received for Canadian Patent Application No. 2626525 (106417-0143), dated Apr. 17, 2013, 4 pages.
Office Action received for Japanese Application No. 2011-520133 (106417-0126), dated Feb. 5, 2014, 4 pages (in Japanese).
Office Action received for Korean Patent Application No. 10-2008-7011791 (106417-0152), dated May 28, 2013, English translation, 3 pages.
Soane,L., et al., "TAT-mediated endocytotic delivery of the loop deletion Bcl-2 protein protects neurons against cell death", Journal of Neurochemistry, (2005), vol. 95, pp. 230-243.
Thomas, et. al., "Progress and Problems with the Use of Viral Vectors for Gene Therapy", Nature, (May 2003), vol. 4, pp. 346-358.
Yagihashi, et al., "Detection of Anti-Survivin Antibody in Gastrointestinal Cancer Patients", Clinical Chemistry, (2001), vol. 47, No. 9, pp. 1729-1731.
Office Action received for Israel Patent Application No. 200919, mailed on Jan. 17, 2013, 4 pages (2 pages of English Translation and 2 pages of Official Copy).
Final Office Action received for U.S. Appl. No. 12/048,148, mailed on Feb. 15, 2013, 17 pages.

(56) References Cited

OTHER PUBLICATIONS

Extended European Search Report and Search Opinion received for Patent Application No. 12187097.6, mailed on Mar. 27, 2013, 8 pages.
Extended European Search Report received for European Patent Application No. 12187077.8, mailed on Mar. 25, 2013, 7 pages.
Office Action received for European Patent Application No. 09747016.5, mailed on Apr. 9, 2013, 6 pages.
Li et al., "Reconstitution of Functional Human B Lymphocytes in NOD/SCID Mice Engrafted with ex vivo Expanded CD34+ Cord Blood Cells", Experimental Hematology, vol. 30, 2002, pp. 1036-1043.
Dang et al., "Nuclear and Nucleolar Targeting Sequences of c-erb-A, c-myb, N-myc, p53, HSP70 and HIV tat Proteins". Journal of Biological Chemistry, vol. 264, No. 30, pp. 18019-18023 (1989).
English Translation of European Search Report for EP Patent Application No. 13188850.0 (1064170161), dated May 27, 2014, 8 pages.
English Translation of Notification of Reasons of Refusal for Japanese Patent Application No. 2012221023 (106417-0151) dated Jun. 24, 2014, 2 pages.
English Translation of Office Action on Israel Patent Application No. 200919 (106576-0125) dated May 19, 2014, 3 pages.
Final Office Action on U.S. Appl. No. 13/795,659 (106417-0136) dated Jul. 11, 2014, 16 pages.
Jayapal et al., "Down-regulation of Myc is Essential for Terminal Erythroid Maturation" The Journal of Biological Chemistry, vol. 285, No. 51, pp. 40252-40265, Dec. 17, 2010.
Notice of Allowance on U.S. Appl. No. 13/777,967 (106417-0107) dated Jul. 14, 2014.
Extended European Search Report received for European Patent Application No. 09747016.5, mailed on May 30, 2012, 8 pages.
Office Action received for Japanese Patent Application No. 2009-553785, mailed on Jun. 19, 2012, 6 pages (2 pages of English Translation and 4 pages of Office Action).
Ju et al., "Anti-Apoptotic Therapy with a Tat Fusion Protein Protects Against Excitotoxic Insults in Vitro and in Vivo", Experimental Neurology, vol. 210, 2008, pp. 602-607.
Australian Search Report and Written Opinion received for Singapore Patent Application No. 201101367-9, mailed on Mar. 23, 2012, 17 pages.
Office Action received for Canadian Patent Application No. 2731767, mailed on Jul. 25, 2012, 3 pages.
Notice of Allowance on U.S. Appl. No. 11/583970, mailed Aug. 29, 2014 (106417-0140).
Office Action received for Chinese Patent Application No. 200680045545.8, mailed on Dec. 31, 2010, 14 pages (8 pages English Translation, 6 Pages Office Action).
Office Action received in Chinese Patent Application No. 2006800455458, mailed Sep. 15, 2011, 16 pages (8 pages of English Machine Translation and 8 pages of Chinese Office Action).
Office Action received for Chinese Patent Application No. 200580031540.5, mailed on Jul. 3, 2012, 19 pages (11 pages English Translation, 8 pages Office Action).
Response to First Office Action filed in Chinese Patent Application No. 200680045545.8 on Jul. 15, 2011, 22 pages (8 pages of English Machine Translation and 14 pages of Chinese-Language Response).
Response to Second Office Action filed in Chinese Patent Application No. 200680045545.8 on Jan. 30, 2012, 23 pages (8 pages of English Machine Translation and 15 pages of Chinese-Language Response).
Request for ReExamination filed in Chinese Patent Application No. 200680045545.8 on Oct. 12, 2012, 23 pages (6 pages of English Machine Translation and 11 pages of Chinese-Language Document as filed).
Office Action received for European Patent Application No. 06826025.6, mailed on Sep. 1, 2009, 3 pages.
Office Action received for European Patent Application No. 06826025.6, mailed on Sep. 22, 2009, 1 page.
Response for European Patent Application No. 09800871.7, filed on Jan. 20, 2012, 5 pages.
Response for European Patent Application No. 09810692.5, filed on Jan. 31, 2012, 7 pages.
Response for European Patent Application No. 09800871.7, filed on Jul. 10, 2012, 5 pages.
Response for European Patent Application No. 09810692.5, filed on Jul. 30, 2012, 5 pages.
Office Action received for Israeli Patent Application No. 190946, mailed on Jul. 3, 2012, 1 page. (English Translation only).
Office Action received for Japanese Patent Application No. 2008-536713, mailed on Jul. 3, 2012, 2 pages (No English Translation Provided).
Response to Office Action filed in Japanese Patent Application No. 2008-536713 on Oct. 3, 2012, 21 pages (11 pages of English Machine Translation and 10 pages of Japanese-Language Response).
Final Office Action Response filed for U.S. Appl. No. 11/583,970 on Jan. 28, 2009, 15 pages.
Final Office Action Response filed for U.S. Appl. No. 11/583,970 on Feb. 4, 2010, 10 pages.
Final Office Action received for U.S. Appl. No. 11/583,970, mailed on Nov. 17, 2011, 16 pages.
Final Office Action received for U.S. Appl. No. 12/701,383, mailed on Nov. 16, 2011, 14 pages.
Final Office Action Response filed for U.S. Appl. No. 12/701,383 on Feb. 15, 2012, 13 pages.
Final Office Action Response filed for U.S. Appl. No. 11/583,970 on Feb. 16, 2012, 14 pages.
Non-Final Office Action Response filed for U.S. Appl. No. 11/583,970 on Aug. 12, 2008, 12 pages.
Non-Final Office Action Response filed for U.S. Appl. No. 11/583,970 on Jun. 24, 2009, 11 pages.
Non Final Office Action received for U.S. Appl. No. 12/701,383, mailed on Apr. 28, 2011, 10 pages.
Non Final Office Action received for U.S. Appl. No. 11/583,970, mailed on May 9, 2011, 11 pages.
Non Final Office Action Response filed for U.S. Appl. No. 12/701,383 Aug. 25, 2011, 20 pages.
Non-Final Office Action Response filed for U.S. Appl. No. 11/583,970 on Aug. 25, 2011, 22 pages.
Restriction Requirement received for U.S. Appl. No. 11/583,970, mailed on Nov. 13, 2007, 14 pages.
Restriction Requirement received for U.S. Appl. No. 12/701,383, mailed on Jan. 25, 2011, 10 pages.
Aubry et al., "N-Myc Shares Cellular Functions with c-Myc", DNA and Cell Biology, vol. 19, No. 6, Jun. 2000, pp. 353-364.
Baum, Christopher, "Insertional Mutagenesis in Gene Therapy and Stem Cell Biology", Current Opinion in Hematology, vol. 14, Jul. 2007, pp. 337-342.
Beerens et al., "Protein Transduction Domains and their Utility in Gene Therapy", Current Gene Therapy, vol. 3, No. 5, 2003, pp. 486-494.
Buske et al., "Deregulated Expression of HOXB4 Enhances the Primitive Growth Activity of Human Hematopoietic Cells", Blood, vol. 100, No. 3, Aug. 1, 2002, pp. 862-868.
Capecchi, Mario R., "Altering the Genome by Homologous Recombination", Science, vol. 244, No. 4910, Jun. 16, 1989, pp. 1288-1292.
Chin et al., "Essential Role for Oncogenic Ras in Tumour Maintenance", Nature, vol. 400, 1999, pp. 468-472.
Choi et al., "Myc Protein is Stabilized by Suppression of a Novel E3 Ligase Complex in Cancer Cells", Genes & Development, vol. 24, 2010, pp. 1236-1241.
Dang, Chi V., "c-Myc Target Genes Involved in Cell Growth, Apoptosis, and Metabolism", Molecular and Cellular . Biology, vol. 19, No. 1, Jan. 1999, pp. 1-11.
Hann et al., "Proteins Encoded by the Human C-Myc Oncogene: Differential Expression in Neoplastic Cells", Mol. Cell. Biol., vol. 4, No. 11, Nov. 1984, pp. 2486-2497.
Merino et al., "Developmental Regulation of the Bcl-2 Protein and Susceptibility to Cell Death in B Lymphocytes", The EMBO Journal, vol. 13, No. 3, 1994, pp. 683-691.
Muchmore et al., "X Ray and NMR Structure of Human Bcl-xL, an Inhibitor of Programmed Cell Death", Nature, vol. 381, May 23, 1996, pp. 335-341.

(56) References Cited

OTHER PUBLICATIONS

Schiedlmeier et al., "High-level Ectopic HOXB4 Expression Confers a Profound in Vivo Competitive Growth Advantage on Human Cord Blood CD34+ Cells, but limpairs Lymphomyeloid Differentiation", Blood, vol. 101, No. 5, Mar. 1, 2003, pp. 1759-1768.
Zhang et al., "Cytokines Regulating Hematopoietic Stem Cell Function", Current Opinion Hematology, vol. 15, No. 4, Jul. 2008, pp. 1-8.
Response for European Patent Application No. 09800871.7, filed on Feb. 6, 2013, 9 pages.
Office Action received for Israeli Patent Application No. 208810, mailed on Jan. 2, 2013, 4 pages (English Translation only).
Office Action received for Australian Patent Application No. 2006304392, mailed on Jul. 16, 2012, 3 pages.
Huettner et al., "Reversibility of Acute B-Cell Leukaemia Induced by BCR-ABL1," Nature Genetics, vol. 24, 2000, pp. 57-60.
Office Action received for Israel Patent Application No. 209968, mailed on Aug. 21, 2012, 4 pages (2 pages of English Translation and 2 pages of Office Action).
Office Action received for Chinese Patent Application No. 200880015602.7, issued on Oct. 31, 2012, 10 pages (6 pages of English Translation and 4 pages of Chinese Office Action).
Office Action received for Canadian Patent Application No. 2,735,522, mailed on Sep. 10, 2012, 3 pages.
Office Action received for Chinese Patent Application No. 200980127166;7, issued on Dec. 5, 2012, 3 pages.
Examination Report on Canadian Application 2,731,767, mailed Sep. 5, 2014 (106417-0121), 2 pages.
English Translation of Decision of Rejection on Japanese Application No. 2011-525258 (106417-0113), mail date Dec. 3, 2014, 11 pages.
Examiner's Report on Canadian Application No. 2680613 (106576-0121) dated Nov. 28, 2014, 4 pages.
Final Office Action on U.S. Appl. No. 12/701,383 (106417-0141) dated Nov. 13, 2014, 18 pages.
Non-Final Office Action on U.S. Appl. No. 13/795,659 (106417-0136) dated Nov. 26, 2014, 13 pages.
Notice of Allowance on U.S. Appl. No. 12/467,957, mailed Nov. 26, 2014 (106576-0103), 7 pages.
Official Action on European Application No. 09810692.5 (106417-0110) dated Oct. 22, 2014, 3 pages.
Bouchard et al., "Control of cell proliferation by Myc", Trends in Cell Biology, vol. 8, pp. 202-206, (1998).
English Translation of Office Action on Israeli Application No. 232432 (106417-0194) dated Mar. 8, 2015, 3 pages.
Examination Report No. 1 on Australian Application No. 2014202016 (106417-0187) dated May 12, 2015, 3 pages.
Examination Report on European Application No. 09747016.5 (106576-0109) dated Mar. 19, 2015, 5 pages.
Examiners Report on Canadian Application No. 2723114 (106576-0107) dated Apr. 21, 2015, 4 pages.
Notice of Acceptance of Australian Application No. 2009246876 (106576-0106) dated Apr. 2, 2015, 3 pages.
Notice of Allowance on U.S. Appl. No. 12/701,383 (106417-0141) dated May 22, 2015, 9 pages.
Pan et al., "Reprogramming human fibroblasts using HIV-1 TAT recombinant proteins OCT4, SOX2, KLF4 and c-MYC," Mol. Biol Rep (2010) 37:2117-2124.
Wechsler et al., "MXI1, a Putative Tumor Suppressor Gene, Suppresses Growth of Human Glioblastoma Cells", Cancer Research 57, pp. 4405-4912, (1997).
Zhang et al., "Reprogramming of somatic cells via TAT-mediated protein transduction of recombinant factors," Biomaterials 33 (2012) 5047-5055.
Re-Examination Report on Australian Patent No. 2009285547 (106417-0105) dated Apr. 23, 2015, 3 pages.
Office Action on Canadian Application No. 2626525 (106417-0143) dated May 8, 2015, 3 pages.
English Translation of Office Action on Israeli Application No. 208810 (106576-0111) dated Jan. 13, 2015, 3 pages.
English Translation of the Third Office Action on Chinese Patent Application No. 200680045545.8 (106417-0144) dated Feb. 15, 2015, 4 pages.
Final Office Action on U.S. Appl. No. 13/795,659 (106417-0136) dated Mar. 26, 2015, 18 pages.
Final Office Action on U.S. Appl. No. 13/797,648 (106417-0174) dated Apr. 1, 2015, 12 pages.
Dvorak et al., "Cytochemical Localization of Peroxidase Activity in the Developing Erythrocyte," Am. J. Pathol. 1972, 67(2), pp. 303-326.
Examination Report on Australian application 2009274172, mailed Jul. 24, 2014 (106417-0120).
International Search Report and Written Opinion for International Application No. PCT/US2014/022971 dated Aug. 13, 2014, 12 pages.
International Search Report and Written Opinion on PCT/US2014/022977, mailed Aug. 28, 2014 (106417-0182).
Notice of Allowance on U.S. Appl. No. 11/583,970, mailed Aug. 29, 2014 (106417-0140).
Xi et al., "In Vitro Large Scale Production of Human Mature Red Blood Cells From Hematopoietic Stem Cells by Coculturing with Human Fetal Liver Stromal Cells," Biomed. Res. Int. Epub Jan. 30, 2013, 2013:807863.
Examiner's Report on European Application No. 12187097.6 (106576-0126) dated Jan. 22, 2015, 6 pages.
International Preliminary Report on Patentability for International Application No. PCT/US2013/051384 (106417-0183), mail date Jan. 29, 2015, 12 pages.
International Search Report and Written Opinion for International Application No. PCT/US2013/051384 (106417-0183), mail date Nov. 13, 2013, 15 pages.
Johnson, N.A. et al., "Lymphomas with concurrent BCL2 and MYC translocations: the critical factors associated with survival", Blood, 2009, vol. 114, No. 11, pp. 2273-2279.
Levesque, J-P et al., "The endosteal 'osteoblastic' niche and its role in hematopoietic stem cell homing and mobilization", Leukemia, 2010, vol. 24, pp. 1979-1992.
Wilson A., et al., c-Myc controls the balance between hematopoietic stem cell self-renewal and differentiation. Genes Dev. 18:2747-63 (2004).

\* cited by examiner

Mouse Red Blood Cells present in the peripheral blood of chimaeric C57/BL6 mice 6 weeks post-BMT.

WT  900R A  900R B  BMT

Mouse Red Blood Cells present in the peripheral blood of chimaeric C57/BL6 mice 6 weeks post-BMT.

SEQUENCE LISTING

<160> NUMBER OF SEQ ID NOS: 1

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
ataacttcgt ataatgtatg ctatacgaag ttat                                34

METHODS FOR PREPARING MATURE ERYTHROCYTES FROM CONDITIONALLY IMMORTALIZED HEMATOPOIETIC STEM CELLS

CROSS-REFERENCE

This application claims priority from U.S. Provisional Application No. 61/082,410, entitled Differentiated Cells and Processes for Preparing the Same, filed 21 Jul. 2008, which is incorporated herein by reference in its entirety.

BACKGROUND OF THE INVENTION

Anucleated cells include, but are not limited to, erythrocytes and thrombocytes. Erythrocytes and thrombocytes are derived from the differentiation of hematopoietic stem cells.

SUMMARY OF THE INVENTION

Disclosed herein, in certain embodiments, is a method of preparing a plurality of anucleated cells comprising: culturing conditionally immortalized stem cells in the presence of at least one cytokine that directs differentiation toward an anucleated cell; wherein the conditionally immortalized stem cells are generated by: (a) transfecting a plurality of stem cells with a first vector comprising: a nucleic acid sequence encoding a MYC molecule; (b) transfecting the stem cells with a second retroviral vector comprising a nucleic acid sequence encoding Bcl-2, Bcl-X, or a combination thereof, and (c) culturing the stem cells with IL-3, IL-6, stem cell factor, thrombopoietin, Flt3 ligand, or a combination thereof, and wherein the activity of the Myc molecule has been suppressed before differentiation. In some embodiments, the cytokine that directs differentiation toward an anucleated cell is IL-3, EPO, or a combination thereof. In some embodiments, the MYC molecule is c-Myc, l-Myc, n-Myc, s-Myc, or a combination thereof. In some embodiments, the first vector further comprises the hormone-binding domain of the human estrogen receptor. In some embodiments, the method further comprises inducing translocation of the Myc molecule to a nucleus. In some embodiments, the method further comprises contacting the plurality of stem cells with: estradiol (E2), 4-hydroxytamoxifen (4-OHT), or both. In some embodiments, the first vector, the second vector, or both the first vector and the second vector is Murine Stem Cell Virus (MSCV), or a derivative thereof. In some embodiments, the first vector, the second vector, or both the first vector and the second vector is MSCV-(IRES)-GFP, or a derivative thereof. In some embodiments, the first vector, the second vector, or both the first vector and the second vector is MSCV-(IRES)-GFP, and further comprises woodchuck hepatitis B virus RNA regulatory element (WRE).

Disclosed herein, in certain embodiments, is a method of producing a plurality of anucleated cells, comprising: culturing conditionally immortalized stem cells in the presence of at least one cytokine that directs differentiation toward an anucleated cell; wherein the conditionally immortalized stem cells are generated by: (a) contacting a plurality of stem cells with an exogenously synthesized first peptide comprising: a MYC molecule that translocates to a nucleus; (b) contacting the stem cells with an exogenously synthesized second peptide comprising: Bcl-2, BCL-X, or a combination thereof; and (c) culturing the stem cells with IL-3, IL-6, stem cell factor, thrombopoietin, Flt3 ligand, or a combination thereof, and wherein the first peptide is removed from contact with the conditionally immortalized stem cells before differentiation. In some embodiments, the first peptide further comprises the hormone-binding domain of the human estrogen receptor. In some embodiments, the first peptide, the second peptide, or both the first and second peptides comprise a transporter sequence. In some embodiments, the first protein, the second protein, or both the first and second proteins comprise a TAT sequence. In some embodiments, the method further comprises contacting the plurality of stem cells with: estradiol (E2), 4-hydroxytamoxifen (4-OHT), or both.

Disclosed herein, in certain embodiments, is a method of preparing a plurality of anucleated cells, comprising: (a) transfecting a plurality of stem cells (e.g., hematopoietic stem cells) with a first vector comprising a nucleic acid sequence encoding a MYC molecule; (b) transfecting the plurality of stem cells (e.g., hematopoietic stem cells) with a second gammaretroviral vector comprising a nucleic acid sequence encoding Bcl-2, Bcl-X, or a combination thereof; (c) culturing the plurality of stem cells (e.g., hematopoietic stem cells) with IL-3, IL-6, stem cell factor, thrombopoietin, Flt3 ligand, or a combination thereof; (d) suppressing the activity of the Myc molecule; and (e) culturing the conditionally immortalized stem cells (e.g., hematopoietic stem cells) in the presence of at least one cytokine that directs differentiation toward an anucleated cell. In some embodiments, the cytokine that directs differentiation toward an anucleated cell is IL-3, EPO, or a combination thereof. In some embodiments, the MYC molecule is c-Myc, l-Myc, n-Myc, s-Myc, or a combination thereof. In some embodiments, the first vector further comprises the hormone-binding domain of the human estrogen receptor. In some embodiments, the method further comprises inducing translocation of the Myc molecule to a nucleus. In some embodiments, the method further comprises contacting the plurality of stem cells (e.g., hematopoietic stem cells) with: estradiol (E2), 4-hydroxytamoxifen (4-OHT), or both. In some embodiments, the first vector, the second vector, or both the first vector and the second vector is Murine Stem Cell Virus (MSCV), or a derivative thereof. In some embodiments, the first vector, the second vector, or both the first vector and the second vector is MSCV-(IRES)-GFP, or a derivative thereof. In some embodiments, the first vector, the second vector, or both the first vector and the second vector is MSCV-(IRES)-GFP, and further comprises woodchuck hepatitis B virus RNA regulatory element (WRE).

Disclosed herein, in certain embodiments, is a method of producing a plurality of anucleated cells (e.g., hematopoietic stem cells), comprising: (a) contacting a plurality of stem cells (e.g., hematopoietic stem cells) with: (i) an exogenously synthesized first peptide comprising: a MYC molecule that translocates to a nucleus; and (ii) an exogenously synthesized second peptide comprising: Bcl-2, BCL-X, or a combination thereof, (b) culturing the plurality of stem cells (e.g., hematopoietic stem cells) with IL-3, IL-6, stem cell factor, thrombopoietin, Flt3 ligand, or a combination thereof; (c) removing the first peptide; and (d) culturing the conditionally immortalized stem cells (e.g., hematopoietic stem cells) in the presence of at least one cytokine that directs differentiation towards an anucleated cell. In some embodiments, the first peptide further comprises the hormone-binding domain of the human estrogen receptor. In some embodiments, the first peptide, the second peptide, or both the first and second peptides comprise a transporter sequence. In some embodiments, the first protein, the second protein, or both the first and second proteins comprise a TAT sequence. In some embodiments, the method further comprises contacting the plurality of stem cells (e.g., hematopoietic stem cells) with: estradiol (E2), 4-hydroxytamoxifen (4-OHT), or both.

Disclosed herein, in certain embodiments, is a thrombocyte prepared according to a method disclosed herein.

Disclosed herein, in certain embodiments, is an erythrocyte prepared according to a method disclosed herein.

Disclosed herein, in certain embodiments, is a method of treating a disorder characterized by a deficiency of anucleated cells, comprising: administering an anucleated cell prepared according to a method disclosed herein. In some embodiments, the disorder is an anemia (e.g., aplastic anemia, pernicious anemia, iron deficiency anemia, sickle cell anemia, spherocytosis, hemolytic anemia), Gaucher's disease, hemolysis, neutropenia, thrombocytopenia, granulocytopenia, hemophilia, Hodgkin's lymphoma, Non-Hodgkin's lymphoma, B cell chronic lymphoma, Burkitt's lymphoma, Follicular-like lymphoma, diffused large B-cell lymphoma, multiple myeloma, acute myeloid leukemia, pre-B acute lymophcytic leukemia, pre-T acute lymphocytic leukemia, acute promeylocytic leukemia, refractory leukemia, or combinations thereof. In certain instances, the disorder characterized by an deficiency in anucleated cells results from (partially or fully) chemotherapy. In some embodiments, an anucleated cell produced by a method disclosed herein is co-administered with chemotherapy.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows a schematic representation of retroviral constructs used to transduce primary murine HSC cells with Myc-ER and Bcl-2. FIG. 1B shows FACS analyses of HSCs obtained from 5-fluorouracil treated donors following the transduction. FIG. 1C shows kinetics of leukemogenesis in mice transplanted with the transduced HSCs. FIG. 1D shows FACS analysis of a ctlt-hematopoietic stem cell soon after recovery from the bone marrow of leukemic mice. FIG. 1E shows FACS analysis of a ctlt-hematopoietic stem cell line that has been established. FIG. 1F shows FACS analysis of stem cell marker in normal, unmanipulated hematopoietic stem cells from the bone marrow of C57/BL6 mice.

FIG. 3A shows the frequency of cells derived from ctlt-hematopoietic stem cells in lymphoid tissues after transplantation. FIG. 3B shows detection of GFP+ myeloid lineage cells in the bone marrow. FIG. 3C shows analysis of peripheral, mature lymphocytes in the spleen. FIG. 3D shows analysis of peripheral, mature lymphocytes in transplant recipient mice following the second serial passage of ctlt-hematopoietic stem cells.

DETAILED DESCRIPTION OF THE INVENTION

Figure 1:
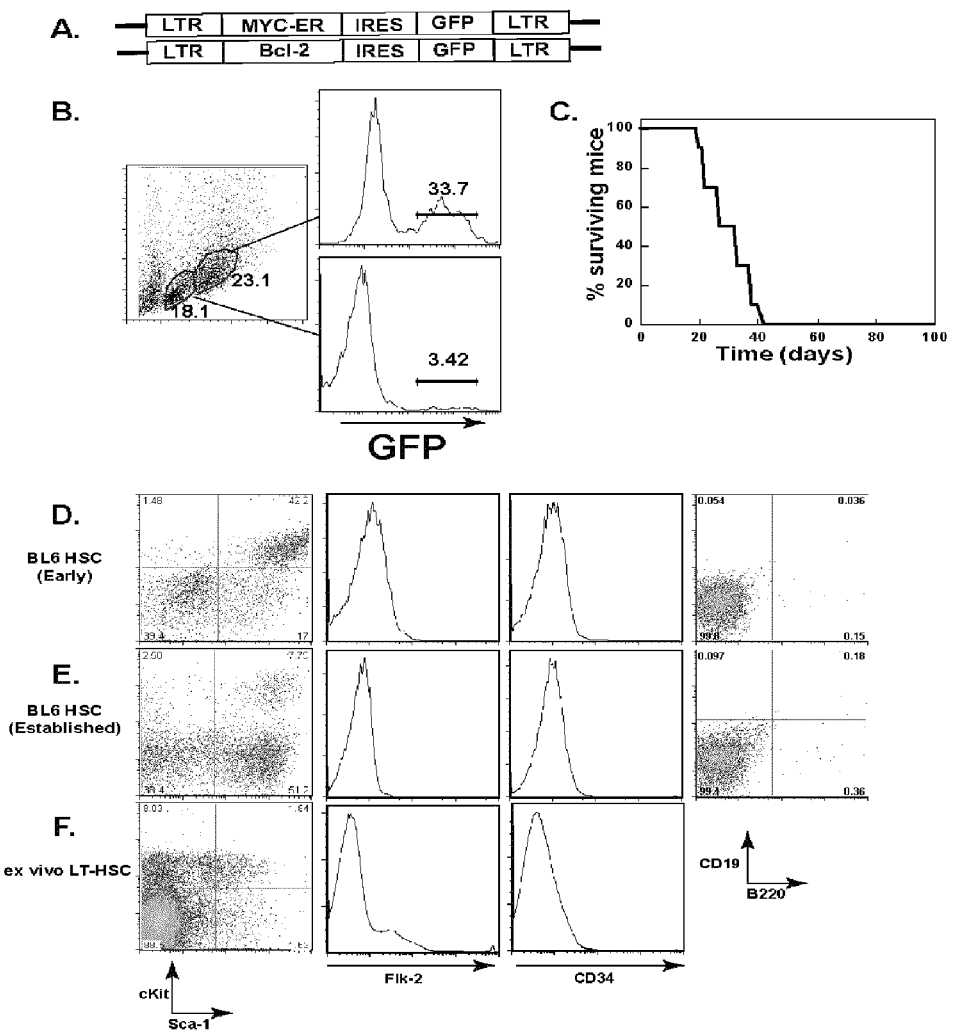
FIG. 1 illustrates an approach for generation of a ctlt-hematopoietic stem cell line.

Disclosed herein are methods for preparing a plurality of anucleated cells, the resulting anucleated cells, and methods for storing and using such anucleated cells. In particular, such anucleated cells are produced ex vivo from stem cells that are either modified with appropriate genes and/or proteins (collectively, an engineered stem cell). Such engineered stem cells are nucleated stem cells, and further are conditionally immortalized. Such engineered, nucleated stem cells provide anucleated cells by causing the cells to lose the conditional immortalization and differentiate as appropriate.

Disclosed herein, in certain embodiments, is a method of preparing a plurality of anucleated cells comprising: culturing conditionally immortalized stem cells in the presence of at least one cytokine that directs differentiation toward an anucleated cell; wherein the conditionally immortalized stem cells are generated by: (a) transfecting a plurality of stem cells with a first vector comprising: a nucleic acid sequence encoding a MYC molecule; (b) transfecting the stem cells with a second retroviral vector comprising a nucleic acid sequence encoding Bcl-2, Bcl-X, or a combination thereof, and (c) culturing the stem cells with IL-3, IL-6, stem cell factor, thrombopoietin, Flt3 ligand, or a combination thereof, and wherein the activity of the Myc molecule has been suppressed before differentiation. In some embodiments, the cytokine that directs differentiation toward an anucleated cell is IL-3, EPO, or a combination thereof. In some embodiments, the MYC molecule is c-Myc, l-Myc, n-Myc, s-Myc, or a combination thereof. In some embodiments, the first vector further comprises the hormone-binding domain of the human estrogen receptor. In some embodiments, the method further comprises inducing translocation of the Myc molecule to a nucleus. In some embodiments, the method further comprises contacting the plurality of stem cells with: estradiol (E2), 4-hydroxytamoxifen (4-OHT), or both. In some embodiments, the first vector, the second vector, or both the first vector and the second vector is Murine Stem Cell Virus (MSCV), or a derivative thereof. In some embodiments, the first vector, the second vector, or both the first vector and the second vector is MSCV-(IRES)-GFP, or a derivative thereof. In some embodiments, the first vector, the second vector, or both the first vector and the second vector is MSCV-(IRES)-GFP, and further comprises woodchuck hepatitis B virus RNA regulatory element (WRE).

Disclosed herein, in certain embodiments, is a method of producing a plurality of anucleated cells, comprising: culturing conditionally immortalized stem cells in the presence of at least one cytokine that directs differentiation toward an anucleated cell; wherein the conditionally immortalized stem cells are generated by: (a) contacting a plurality of stem cells with an exogenously synthesized first peptide comprising: a MYC molecule that translocates to a nucleus; (b) contacting the stem cells with an exogenously synthesized second peptide comprising: Bcl-2, BCL-X, or a combination thereof; and (c) culturing the stem cells with IL-3, IL-6, stem cell factor, thrombopoietin, Flt3 ligand, or a combination thereof, and wherein the first peptide is removed from contact with the conditionally immortalized stem cells before differentiation. In some embodiments, the first peptide further comprises the hormone-binding domain of the human estrogen receptor. In some embodiments, the first peptide, the second peptide, or both the first and second peptides comprise a transporter sequence. In some embodiments, the first protein, the second protein, or both the first and second proteins comprise a TAT sequence. In some embodiments, the method further comprises contacting the plurality of stem cells with: estradiol (E2), 4-hydroxytamoxifen (4-OHT), or both.

Disclosed herein, in certain embodiments, is a method of preparing a plurality of anucleated cells, comprising: (a) transfecting a plurality of stem cells (e.g., hematopoietic stem cells) with a first vector comprising a nucleic acid sequence encoding a MYC molecule; (b) transfecting the plurality of stem cells (e.g., hematopoietic stem cells) with a second gammaretroviral vector comprising a nucleic acid sequence encoding Bcl-2, Bcl-X, or a combination thereof; (c) culturing the plurality of stem cells (e.g., hematopoietic stem cells) with IL-3, IL-6, stem cell factor, thrombopoietin, Flt3 ligand, or a combination thereof; (d) suppressing the activity of the Myc molecule; and (e) culturing the conditionally immortalized stem cells (e.g., hematopoietic stem cells) in the presence of at least one cytokine that directs differentiation toward an anucleated cell. In some embodiments, the cytokine that directs differentiation toward an anucleated cell is IL-3, EPO, or a combination thereof. In some embodiments, the MYC molecule is c-Myc, l-Myc, n-Myc, s-Myc, or a combination thereof. In some embodiments, the first vector further comprises the hormone-binding domain of the human estrogen receptor. In some embodiments, the method further comprises inducing translocation of the Myc molecule to a nucleus. In some embodiments, the method further comprises contacting the plurality of stem cells (e.g., hematopoietic stem cells) with: estradiol (E2), 4-hydroxytamoxifen (4-OHT), or both. In some embodiments, the first vector, the second vector, or both the first vector and the second vector is Murine Stem Cell Virus (MSCV), or a derivative thereof. In some embodiments, the first vector, the second vector, or both the first vector and the second vector is MSCV-(IRES)-GFP, or a derivative thereof. In some embodiments, the first vector, the second vector, or both the first vector and the second vector is MSCV-(IRES)-GFP, and further comprises woodchuck hepatitis B virus RNA regulatory element (WRE).

Disclosed herein, in certain embodiments, is a method of producing a plurality of anucleated cells (e.g., hematopoietic stem cells), comprising: (a) contacting a plurality of stem cells (e.g., hematopoietic stem cells) with: (i) an exogenously synthesized first peptide comprising: a MYC molecule that translocates to a nucleus; and (ii) an exogenously synthesized second peptide comprising: Bcl-2, BCL-X, or a combination thereof, (b) culturing the plurality of stem cells (e.g., hematopoietic stem cells) with IL-3, IL-6, stem cell factor, thrombopoietin, Flt3 ligand, or a combination thereof; (c) removing the first peptide; and (d) culturing the conditionally immortalized stem cells (e.g., hematopoietic stem cells) in the presence of at least one cytokine that directs differentiation towards an anucleated cell. In some embodiments, the first peptide further comprises the hormone-binding domain of the human estrogen receptor. In some embodiments, the first peptide, the second peptide, or both the first and second peptides comprise a transporter sequence. In some embodiments, the first protein, the second protein, or both the first and second proteins comprise a TAT sequence. In some embodiments, the method further comprises contacting the plurality of stem cells (e.g., hematopoietic stem cells) with: estradiol (E2), 4-hydroxytamoxifen (4-OHT), or both.

Disclosed herein, in certain embodiments, is a thrombocyte prepared according to a method disclosed herein.

Disclosed herein, in certain embodiments, is an erythrocyte prepared according to a method disclosed herein.

Disclosed herein, in certain embodiments, is a method of treating a disorder characterized by a deficiency of anucleated cells, comprising: administering an anucleated cell prepared according to a method disclosed herein.

Provided in certain embodiments herein is a method for producing a plurality of differentiated cells. In some embodiments, provided herein is a method for producing a plurality of anucleated cells, comprising:
 (a). providing an immortalized stem cell; and
 (b). inducing differentiation of the immortalized stem cell to the cell of a selected type.

GENERAL DEFINITIONS

Any methods and materials similar or equivalent to those described herein that is used in the practice of or testing of the embodiments described herein are considered to be a part of the instant disclosure.

As used in this specification and the appended claims, the singular forms "a", "an", and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth. Any reference to "or" herein is intended to encompass "and/or" unless otherwise stated.

As used herein, "stem cells (e.g., hematopoietic stem cells)" refers to the term as it is generally understood in the art. For example, stem cells (e.g., hematopoietic stem cells), regardless of their source, are cells that are capable of dividing and renewing themselves for long periods, are unspecialized (undifferentiated), and possess the ability to give rise to (differentiate into) specialized cell types (i.e., they are progenitor or precursor cells for a variety of different, specialized cell types). In certain instances herein, "stem cells (e.g., hematopoietic stem cells)" described herein refer to long term stem cells (e.g., hematopoietic stem cells).

"Long-term", when used in connection with stem cells (e.g., hematopoietic stem cells), refers to the ability of stem cells (e.g., hematopoietic stem cells) to renew themselves by dividing into the same non-specialized cell type over long periods (e.g., 1 month, 2 months, 3 months, 4 months, 6 months, 8 months, 9 months, 12 months, 2 years, 3 years) depending on the specific type of stem cell. In certain instances, stem cells (e.g., hematopoietic stem cells) are identified by the presence of the following cell surface markers: c-kit$^+$, Sca-1$^+$, CD34$^{low/-}$, CD38$^+$, and/or Thy1$^{+/low}$. In some instances, human stem cells (e.g., hematopoietic stem cells) are identified by the presence of the following markers: CD34$^+$, CD38$^{low/-}$, c-kit$^{-/low}$, and/or Thy1$^+$. In certain instances, both human and murine stem cells (e.g., hematopoietic stem cells) lack cell lineage markers, such as CD2, CD3, CD4, CD5, CD8, NK1.1, B220, Ter-119, and/or Gr-1.

An "immortalizing agent" as used herein refers to an agent that induces, promotes, or enables cell viability, cell survival, and/or cell proliferation. An "immortalizing agent" refers to any suitable agent that induces, promotes, or enables cell viability, cell survival, and/or cell proliferation. The term encompasses all chemical compounds that induce cell viability, cell survival, and/or cell proliferation, such as organic and inorganic molecules, including DNA, RNA, polypeptides, carbohydrates, lipids, and small organic molecules.

A "conditionally activated agent that induces immortality" refers to an agent that induces cell viability, cell survival, and/or cell proliferation, whose function is induced or initiated as necessary. For example, in the case of polypeptides, conditional activation occurs by activating, e.g., expression, transcription, or translation of a gene encoding the polypeptide. In other cases, the function of a conditionally activated polypeptide is induced by adding a ligand to a receptor on the polypeptide, e.g., exposing a polypeptide comprising ER to estrogen or a polypeptide comprising GR to mifepristone.

The term "onco-peptide" and "oncoprotein" are utilized interchangeably herein and refer to a polymer of amino acid residues, fragments or analogs thereof that are encoded by oncogenes or proto-oncogenes. In certain instances, onco-peptides induce cell viability, cell survival and/or cell proliferation. The description of certain embodiments herein is directed to "onco-peptides". It is to be understood that in some embodiments, such disclosures include a disclosure of the use of any polypeptide that induces stem cell viability, survival and/or proliferation.

"An inhibitor of an endogenous antagonist of an immortalizing agent" refers to an agent that induces cell immortality by reducing, decreasing, or preventing the activity, concentration, or expression of an endogenous agent that antagonizes an immortalizing agent. For example, certain endogenous transcription repressors suppress expression of polypeptides that function to induce cell viability, cell survival, and/or cell proliferation. A specific example is the MAD family of transcription repressors, e.g., MAD-1, which antagonize the Myc family of oncogenes. Thus, an inhibitor of an endogenous transcription repressor, e.g., MAD-1, functions to induce cell immortality by reducing, decreasing, or preventing the activity, concentration, or level of the transcription repressor.

In other embodiments, for example, an inducer of cell immortality is a cyclin-dependent kinase. Endogenous cyclin-dependent kinase inhibitors, e.g., p16, p19, p21, and p27, function to antagonize the promotion of cell immortality by the cyclin-dependent kinases. Thus, in some embodiments, "an inhibitor of an endogenous antagonist of an inducer of cell immortality" is an agent that reduces, decreases, or prevents the activity, concentration, or level of the cyclin-dependent kinase inhibitors relative to a wild-type stem cell of the same type.

Similarly, an "inhibitor of pro-apoptotic polypeptides" functions to induce cell immortality by reducing, decreasing, or preventing the activity, concentration, or level of polypeptides, e.g., endogenous polypeptides, that are pro-apoptotic. "Inhibitors of pro-apoptotic polypeptides" reduce, decrease, or prevent the activity, concentration, or level of pro-apoptotic polypeptides by any suitable means, including inhibiting expression, transcription, or translation of the polypeptides, or directly acting on the polypeptides, e.g., by binding to the polypeptides, denaturing the polypeptides, occupying the active site of the polypeptides, or blocking interaction of the polypeptides with their targets.

In certain embodiments, homologues, analogues or fragments of polypeptides that induce immortality described herein include an amino acid sequence that is at least 40% to 100% identical, e.g., at least 40%, 45%. 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the polypeptide that induces immortality.

As used herein, the terms "Myc", "cMyc", "Myc protein" and "Myc polypeptide" are used interchangeably and refers in certain instances to the NCBI Accession Number NP002458.2, functional homologs, analogs or fragments thereof. In some embodiments, synonyms of Myc include, but are not limited to c-Myc, v-Myc, Myc proto-oncogene protein & Transcription factor p64. In some embodiments, a Myc polypeptide comprises an amino acid sequence that is at least 40% to 100% identical, e.g., at least 40%, 45%. 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the sequence of NCBI Accession Numbers NP002458.2. In some embodiments, a Myc polypeptide comprises a polypeptide sequence of 40 amino acids or more in length that is at least 50% to 100% identical, e.g., at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the sequence of NCBI Accession Numbers NP002458.2. In some embodiments, a Myc polypeptide comprises a polypeptide sequence of 40 amino acids or more in length that is at least 50% to 100% identical, e.g., at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the sequence of NCBI Accession Numbers NP002458.2 wherein the Myc polypeptide induces cell viability, cell immortality, cell growth and/or cell proliferation.

To determine the percent homology of two amino acid sequences or of two nucleic acids, the sequences is aligned for optimal comparison purposes (e.g., gaps are introduced in the sequence of a first amino acid or nucleic acid sequence for optimal alignment with a second amino acid or nucleic acid sequence). The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In some embodiments the two sequences are the same length.

To determine percent homology between two sequences, the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877 is used. Such an algorithm is incorporated into the NBLAST and XBLAST programs of Altschul, et al. (1990) *J. Mol Biol.* 215:403-410. BLAST nucleotide searches is performed with the NBLAST program, score=100, wordlength=12 to obtain nucleotide sequences homologous to a nucleic acid molecules described or disclose herein. BLAST protein searches is performed with the XBLAST program, score=50, wordlength=3. To obtain gapped alignments for comparison purposes, Gapped BLAST is utilized as described in Altschul et al. (1997) *Nucleic Acids Res.* 25:3389-3402. When utilizing BLAST and Gapped BLAST programs, the default parameters of the respective programs (e.g., XBLAST and NBLAST) are used. See the website of the National Center for Biotechnology Information for further details (on the World Wide Web at ncbi.nlm.nih.gov). Proteins suitable for use in the methods described herein also includes proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 77%, 80%, 82%, 85%, 88%, 90%, 92%, 95%, 97%, 98%, 99%, or 100% identical to the amino acid sequence of any protein inhibitor described herein. Such sequence-variant proteins are suitable for the methods described herein as long as the altered amino acid sequence retains sufficient biological activity to be functional in the compositions and methods described herein. In certain instances conservative amino acid substitutions are utilized. Illustrative conservative substitution among amino acids are within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al. (1992), *Proc. Natl Acad. Sci. USA,* 89:10915-10919). The BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

As used herein, the term "nucleic acid" refers to a nucleic acid that is engineered through the combination or insertion of one or more nucleic acids, thereby combining sequences that would not normally occur together in nature. In some embodiments, nucleic acids comprise inducers or enhancers. In some embodiments, nucleic acids comprise restriction enzyme sites. In some embodiments, nucleic acids encode polypeptides. In some embodiments, nucleic acids comprise mutations.

As used herein, the term "polypeptide" refers to a polypeptide that is produced from a nucleic acid.

As used herein, the term "Myc polypeptide" comprises a Myc polypeptide that is produced from a nucleic acid.

As used herein, the term "transgene" refers to the integration of a nucleic acid that encodes a polypeptide into the genomic DNA of an animal, bacteria, virus or cell.

As used herein, the term "TRE" refers to a tetracycline response element.

As used herein, "over-expression", refers to a higher level of expression when compared to the endogenous level of expression of an identical polypeptide or protein within the same cell. In certain instances, "over-expression" refers to expression of a polypeptide. In some embodiments a higher level of expression comprises 2% to 200% higher. In some embodiments a higher level of expression comprises 2-fold to 1000-fold higher. In some embodiments a higher level of expression comprises 2-fold to 1000-fold higher. In some embodiments a higher level of expression comprises 2-fold to 10,000-fold higher. In some embodiments a higher level of expression comprises a detectable level of expression when compared to a previous undetectable level of expression. In some embodiments "over-expression" refers to any detectable level of expression of an exogenous polypeptide or protein.

The terms "polypeptide", "peptide" and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins, wherein the amino acid residues are linked by covalent peptide bonds.

I. Immortalized Cells

Stem Cells

Stem cells (e.g., hematopoietic stem cells) to be immortalized or conditionally immortalized are obtained from any suitable source. In certain embodiments, the stem cells (e.g., hematopoietic stem cells) utilized are from an animal, e.g., a human, dog, cat, horse, cow, pig, sheep, goat, chicken, monkey, rat, mouse, or the like. In some embodiments, a stem cell is obtained from the bone marrow, peripheral blood, umbilical cord, or fetal tissue of an individual or is procured from a source that obtained a stem cell from the bone marrow, peripheral blood, umbilical cord, or fetal tissue of an individual.

In certain embodiments, the plurality of stem cells (e.g., hematopoietic stem cells) is harvested from a human umbilical cord or placenta. Another source of a plurality of stem cells (e.g., hematopoietic stem cells) is the developing blood-producing tissues of fetal animals. In human, the plurality of stem cells (e.g., hematopoietic stem cells) is found in the circulating blood of a human fetus by about 12 to 18 weeks. In some embodiments, the a plurality of stem cells (e.g., hematopoietic stem cells) are obtained from any source, e.g., the bone marrow, umbilical cord, peripheral blood, or fetal tissue of blood, of type A+, A−, B+, B−, O+, O−, AB+, and AB− donors. In some embodiments, a plurality of stem cells (e.g., hematopoietic stem cells) are obtained by anesthetizing the stem cell donor, puncturing the posterior superior iliac crest with a needle, and performing aspiration of bone marrow cells with a syringe.

Further steps involved in the processing of remaining marrow cells comprises cell collection by centrifugation, resuspension of cells in culture medium or a buffer suitable for subsequent processing. In some embodiments, the plurality of stem cells (e.g., hematopoietic stem cells) is harvested from circulating blood. In some embodiments, a plurality of stem cells (e.g., hematopoietic stem cells) in the bone marrow are coaxed to migrate from marrow to circulating blood in greater numbers by injecting the stem cell donor with a cytokine, such as granulocyte-colony stimulating factor (G-CSF).

In certain aspects described herein, the plurality of stem cells (e.g., hematopoietic stem cells) is obtained from different blood groups or major histocompatibility complex (MHC) or human leukocyte antigen (HLA) matching source. In some embodiments, drawing from the peripheral blood comprises injection of granulocyte stimulating factor (G-CSF) a few days before the cell harvest. In some embodiments, obtaining a plurality of stem cells (e.g., hematopoietic stem cells) comprises drawing a plurality of stem cells (e.g., hematopoietic stem cells) from the bone marrow comprises injection of 5-fluorouracil (5-FU) in order to enrich for a plurality of stem cells (e.g., hematopoietic stem cells) by inducing these cells to proliferate.

Any suitable identification method is optionally utilized to identify a stem cell obtained from a donor. For example, in some embodiments, identification of a plurality of stem cells (e.g., hematopoietic stem cells) comprises using cell surface markers associated with a plurality of stem cells (e.g., hematopoietic stem cells) or specifically associated with terminally differentiated cells of the system. In one embodiment, markers include one or more of c-kit, Sca-1, CD34, CD38, Thy1, CD2, CD3, CD4, CD5, CD8, CD43, CD45, CD59, CD90, CD105, CD133, ABCG2, NK1.1, B220, Ter-119, Flk-2, CDCP1, Endomucin, or Gr-1. In another embodiment, markers include one or more of CD 150, CD244 or CD46.

A plurality of stem cells (e.g., hematopoietic stem cells) obtained from a donor are separated from non-a plurality of stem cells (e.g., hematopoietic stem cells) in any suitable manner such as, by way of non-limiting example, fluorescence activated cell sorting (FACS), or magnetic activated cell sorting (MACS).

In one non-limiting example, murine bone marrow cells are incubated with antibodies recognizing cell surface molecules such as one or more of c-kit, Sca-1, CD34, CD38, Thy1, CD2, CD3, CD4, CD5, CD8, CD43, CD45, CD59, CD90, CD105, CD133, ABCG2, NK1.1, B220, Ter-119, Flk-2, CDCP1, Endomucin, or Gr-1. Antibodies for CD2, CD3, CD4, CD5, CD8, NK1.1, B220, Ter-119, and Gr-1 are conjugated with magnetic beads. In MACS equipment, the cells harboring CD2, CD3, CD4, CD5, CD8, NK1.1, B220, Ter-119, or Gr-1 on their surface are retained in the column equipped to trap magnetic beads and the cells attached to magnetic bead conjugated antibodies. The cells that are not captured by MACS column are subjected to FACS analysis. For FACS analysis, Antibodies for surface molecules such as c-kit, Sca-1, CD34, CD38, Thy1, are conjugated with fluorescent materials. The cells that are c-kit$^+$, Sca-1$^+$, CD34$^{low/-}$, CD38$^+$, Thy1$^{+/low}$ are separated from the rest of sample by virtue of the types of fluorescent antibodies associated with the cells. These cells are provided as murine long term stem cells (e.g., hematopoietic stem cells) for further method as described herein. In other embodiments, different sets of marker are used to separate murine long term stem cells (e.g., hematopoietic stem cells) from cells of bone marrow, umbilical cord blood, fetal tissue, and peripheral blood.

In another non-limiting example, human peripheral blood cells are incubated with antibodies recognizing c-kit, Sca-1, CD34, CD38, Thy1, CD2, CD3, CD4, CD5, CD8, CD43, CD45, CD59, CD90, CD105, CD133, ABCG2, NK1.1, B220, Ter-119, Flk-2, CDCP1, Endomucin, or Gr-1. Antibodies for CD2, CD3, CD4, CD5, CD8, NK1.1, B220, Ter-119, and Gr-1 are conjugated with magnetic beads. The cells expressing CD2, CD3, CD4, CD5, CD8, NK1.1, B220, Ter-119, or Gr-1 are retained in the column equipped to trap magnetic beads and cells attached to magnetic bead conjugated antibodies. The cells that are not captured by the MACS column are subjected to FACS analysis. Antibodies for c-kit, Sca-1, CD34, CD38, Thy1, are conjugated with fluorescent materials known in the art. The cells that are CD34$^+$, CD38$^{low/-}$, c-kit$^{-/low}$, Thy1$^+$ are separated from the rest of sample by virtue of the types of fluorescent antibodies associated with the cells. These cells are provided as human long term stem cells (e.g., hematopoietic stem cells) for further method disclosed herein.

In yet another non-limiting example, cells obtained from a subject are labeled with the same set of magnetic bead conjugated antibodies (antibodies against one or more of CD2, CD3, CD4, CD5, CD8, NK1.1, B220, Ter-119, or Gr-1) and fluorescent conjugated CD150, CD244 and/or CD48 antibodies. After removing cells captured by the magnetic bead conjugated antibodies from the sample, the sample is analyzed by FACS and CD150+, CD244– and CD48– cells are retained as long term stem cells (e.g., hematopoietic stem cells).

In some embodiments, a plurality of stem cells (e.g., immortalized or stem cells) utilized in any method described herein comprise one or more of the markers: c-kit$^+$, Sca-1$^+$, CD34$^{low/-}$, CD38$^+$, Thy1$^{+/low}$, CD34$^+$, CD38$^{low/-}$, c-kit$^{-/low}$, and/or Thy1$^+$. In some embodiments, the stem cells (e.g., immortalized or stem cells) utilized in any method described herein lack one or more of the markers: CD2, CD3, CD4, CD5, CD8, NK1.1, B220, Ter-119, and/or Gr-1. In certain embodiments, the stem cells (e.g., immortalized or stem cells) utilized in any method described herein are of an A+, A–, B+, B–, O+, O–, AB+, or AB– type.

In some embodiments, providing an immortalized stem cell includes providing at least one immortalized or stem cell. In certain embodiments, providing at least one immortalized stem cell includes providing a plurality of immortalized or stem cells (e.g., hematopoietic stem cells). In some embodiments, providing an immortalized stem cell comprises producing an immortalized or stem cell. In specific embodiments, providing an immortalized stem cell comprises producing a plurality of immortalized or stem cells (e.g., hematopoietic stem cells). In other embodiments, the immortalized or stem cell(s) are provided by procuring them from any source.

Immortalization

In certain embodiments, the conditionally immortalized stem cells (e.g., hematopoietic stem cells) are continuously maintained under suitable conditions for a suitable period of time, successfully becoming an establishing an immortalized or conditionally immortalized stem cell line.

In certain embodiments, inducing proliferation of a conditionally immortalized stem cell according to any method described herein includes inducing immortalization of the conditionally immortalized stem cell and thereby causing the conditionally immortalized stem cells (e.g., hematopoietic stem cells) to proliferate. In some embodiments, inducing proliferation comprises inducing expression of an agent that induces immortality. In certain embodiments, expression of an agent that induces immortality is induced in a conditionally immortalized cell comprising a transgene encoding the agent that induces immortality, wherein the transgene encoding the immortalizing agent is one or more TREs.

In certain embodiments, an immortalized stem cell is, by way of non-limiting example, an immortalized hematopoietic stem cell, an immortalized mesenchymal stem cell, an immortalized neural stem cell, an immortalized epithelial stem cell, an immortalized intestinal stem cell, an immortalized cardiac myocyte progenitor stem cell, an immortalized skin stem cell, an immortalized follicular stem cell, an immortalized skeletal muscle stem cell, an immortalized osteoblastic precursor stem cell, an immortalized liver stem cell, an immortalized embryonic stem cell or the like. In specific embodiments, the immortalized stem cell is an immortalized hematopoietic stem cell.

In some embodiments, the immortalized stem cell is produced by contacting a conditionally immortalized stem cell with an agent that induces immortality. In some embodiments, immortalization of the conditionally immortalized stem cell obviates the inability of a normal or wild type stem cell of the same lineage to survive, proliferate and/or differentiate ex vivo after an extended period of time (e.g., more than 6 hours, 12 hours, 24 hours, 3 days, 1 week, 2 weeks, 1 month, 3 months, etc.). In certain embodiments, the immortalizing agents are conditionally activated.

In some embodiments, the immortalizing agent is an oncopeptide that induces immortality. For example, in certain embodiments, suitable onco-peptides that induce immortality are: growth factors and/or mitogens, receptor tyrosine kinases, particularly constitutively active receptor tyrosine kinases, cytoplasmic tyrosine kinases, cytoplasmic serine/threonine kinases and their regulatory subunits, regulatory GTPases, transcription factors, telomerase reverse transcriptases, and/or factors that activate other onco-peptides. In some embodiments, the immortalized stem cell has been modified to express or conditionally express the onco-peptide. Furthermore, in some embodiments, the function or expression of the onco-peptide is conditionally activated.

In some embodiments, the immortalizing agent inhibits an endogenous antagonist of an inducer of immortality. For example, in some embodiments, an agent that induces immortality comprises an inhibitor of a transcriptional repressor that antagonizes expression of a gene that induces immortality. In certain embodiments, the transcriptional repressor antagonizes an onco-peptide, e.g., Myc.

In some embodiments, an agent that induces immortality is a polypeptide that inhibits apoptosis, e.g., an anti-apoptotic polypeptide. In some embodiments, the immortalized stem cell expresses and/or conditionally expresses a polypeptide that inhibits apoptosis, e.g., the cell comprises a transgene expressing or conditionally expressing a polypeptide that inhibits apoptosis. In some embodiments, an agent that induces immortality is an agent that inhibits pro-apoptotic polypeptides, e.g., endogenous pro-apoptotic polypeptides.

In some embodiments, an immortalized or conditionally immortalized stem cell is generated by contacting a stem cell with an agent that induces immortality, (e.g., an onco-peptide or transgene expressing or over-expressing an onco-peptide). In some embodiments, an immortalized or conditionally immortalized stem cell is generated by contacting a stem cell with an agent that induces immortality, (e.g., an onco-peptide or transgene expressing or over-expressing an onco-peptide), in combination with at least one other agent selected from an agent that: induces immortality, (e.g., another onco-peptide, and/or another transgene expressing or over-expressing an onco-peptide), an inhibitor of an endogenous antagonist of an inducer of cell immortality, an anti-apoptotic polypeptide, an inhibitor of pro-apoptotic polypeptides, or a combination thereof.

Immortalized or conditionally immortalized stem cells (e.g., hematopoietic stem cells) utilized in a method described herein are prepared in any suitable manner. In some embodiments, a conditionally immortalized stem cell is produced by contacting the conditionally immortalized stem cell with a polypeptide and/or a transgene (e.g., an oncogene or proto-oncogene) encoding a polypeptide that induces immortality. In certain embodiments, the conditionally immortalized stem cell is produced by contacting the conditionally immortalized stem cell with an onco-peptide (e.g., Myc) and/or a transgene encoding an onco-peptide (e.g., Myc). In some embodiments wherein the immortalized or conditionally immortalized stem cells (e.g., hematopoietic stem cells) utilized in method described herein comprise a transgene that encodes an onco-peptide, any method described herein optionally further comprises excising the transgene from the nucleus of either the immortalized or conditionally immortalized stem cell prior to differentiation, or from the nucleus of the cell of a selected type following differentiation.

Delivery of a transgene encoding an agent that induces immortality, e.g., an onco-peptide, an anti-apoptotic polypeptide, an inhibitor of a pro-apoptotic polypeptide or endogenous antagonist of an inducer of cellular immortality, etc., into a stem cell is achieved in any suitable manner. In certain instances, a transgene encoding an agent that induces immortality is transfected into a stem cell using a vector. Inserting the nucleic acid into a cell, as used herein, optionally comprises, by way of non-limiting example, microinjection, gene transfection, gene transduction, electroporation or like methods. In some instances, a transgene encoding an agent that induces immorality is transduced into the conditionally immortalized stem cell. In some embodiments, the method of transfecting or transducing a transgene encoding an agent that induces immortality into a stem cell is as set forth in U.S. 2007/0116691, which is hereby incorporated by reference for this disclosure. Delivery of a polypeptide that induces immortality, e.g., an onco-peptide, an anti-apoptotic polypeptide, an inhibitor of a pro-apoptotic polypeptide or endogenous antagonist of an inducer of cellular immortality, etc., into a stem cell is achieved in any suitable manner. In some embodiments, the polypeptide is introduced into the cell by expression of a transgene encoding the polypeptide. In certain embodiments, the polypeptide is a fusion polypeptide comprising a polypeptide transduction domain and the polypeptide is introduced into the conditionally immortalized stem cell by culturing the conditionally immortalized stem cell with the fusion polypeptide. In some embodiments, the method of introducing a polypeptide into a stem cell is as set forth in U.S. 2007/0116691, which is hereby incorporated by reference for this disclosure.

In some embodiments, an immortalized stem cell utilized in any method described herein comprises an agent that induces cell immortality. In some embodiments, an agent that induces cell immortality comprises a transgene that expresses or over-expresses a polypeptide that induces cell immortality. In some embodiments, an agent that induces cell immortality comprises a polypeptide that induces cell immortality. In some embodiments, a polypeptide that induces cell immortality is an onco-peptide. Onco-peptides are of any suitable class that induces cell immortality. For example, in certain embodiments, suitable onco-peptides that induce cell immortality are: growth factors and/or mitogens (e.g., PDGF-derived growth factors such as c-Sis); receptor tyrosine kinases, particularly constitutively active receptor tyrosine kinases (e.g., epidermal growth factor receptor (EGFR), thrombocyte-derived growth factor receptor (PDGFR), vascular endothelial growth factor receptor (VEGFR), and HER2/neu); cytoplasmic tyrosine kinases (e.g., Src-family, Syk-ZAP-70 family, and BTK family of tyrosine kinases); cytoplasmic serine/threonine kinases and their regulatory subunits (e.g., Raf kinases, cyclin-dependent kinases, members of the Akt family); regulatory GTPases (e.g., Ras protein); transcription factors (e.g., Myc and HIF-1a); telomerase reverse transcriptases (e.g., TERT or hTERT); and/or factors that activate other onco-peptides (e.g. cyclins, including cyclins A, B, D, and/or E, such as cyclin D1 and D3). In certain embodiments, an onco-peptide is Myc, HIF-1a, Notch-1, Akt, hTERT, or a cyclin. In some embodiments, an onco-peptide is a functional fragment, homolog, or analogue of any onco-peptide that induces cell viability, cell survival and/or cell proliferation, e.g., a functional fragment, homologue, or analogue of Myc, HIF-1a, Notch-1, Akt, hTERT, or a cyclin.

In some embodiments, an agent that induces cell immortality inhibits an endogenous antagonist of an inducer of cell immortality. For example, the agent is a genetic inhibitor or a small molecule inhibitor (such as, an antagonist). For example, in some embodiments, an agent that induces cell immortality comprises an inhibitor of a transcriptional repressor that suppresses expression of a gene that induces cell immortality. In certain embodiments, the transcriptional repressor antagonizes an onco-peptide that regulates expression of a gene that induces cell immortality, e.g., Myc. For example, in some embodiments, an agent that induces cell immortality comprises an agent that inhibits at least one member of the MAD family of transcriptional repressors, e.g., MAD-1. In certain other embodiments, an agent that induces cell immortality comprises an inhibitor of cyclin-dependent kinase inhibitors (e.g., p16, p19, p21, or p27).

Any agent that inhibits an endogenous antagonist of an agent that induces cell immortality relative to a wild-type stem cell of the same type is suitable for use in the method disclosed herein. An agent that is an inhibitor of an endogenous antagonist of an agent that induces cell immortality reduces, inhibits, or decreases the activity or level of the antagonist at any stage or by any mechanism. For example, in some instances, such an agent interferes with expression of an agent that antagonizes the activity of an agent that induces cell immortality, e.g., at the translational level or at the transcriptional level. In certain embodiments, an agent that interferes with expression of an agent that antagonizes the activity of an agent that induces cell immortality is an agent capable of RNA interference (an RNAi molecule). In some embodiments, an RNAi molecule is generated by cleavage of or binding to mRNA encoding a polypeptide, e.g., an onco-peptide. An RNAi molecule is generated by any suitable means, including by small interfering RNA (siRNA), microRNA (miRNA), double stranded RNA (dsRNA), or small hairpin RNA (shRNA). In certain embodiments, an agent that interferes with expression of an agent that antagonizes the activity of an agent that induces cell immortality is a small molecule, e.g., a small organic molecule.

In some embodiments, an agent that inhibits an endogenous antagonist of an agent that induces cell immortality acts directly on the antagonist. For example, in some embodiments, an agent that induces cell immortality comprises an agent that binds to and inhibits the activity of an endogenous antagonist of an agent that induces cell immortality, such as an antibody or small molecule. For example, in some embodiments, a suitable agent is an agent that binds to or interferes with an antagonist of an onco-peptide, such as antibodies or small molecules that bind to and disrupt the natural function of one or more of the MAD family of transcriptional repressors (e.g., MAD-1) or cyclin-dependent kinase inhibitors (e.g., p16, p19, p21, or p27).

In some embodiments, an agent that induces cell immortality is a transgene that expresses or over-expresses an anti-apoptotic polypeptide. In some embodiments, an agent that induces cell immortality is an anti-apoptotic polypeptide. In some embodiments, the anti-apoptotic polypeptide in a stem cell or stem expressed by a cell comprises one or more of a Bcl-2 homology domain. In some specific embodiments, the anti-apoptotic polypeptide comprising one or more of a Bcl-2 homology domain (e.g., BH1, BH2, BH3 and/or BH4) is e.g., Bcl-2, Bcl-x, Bcl-XL, Mcl-1, CED-9, A1, Bfl-1, Bcl-w, or the like.

In some embodiments, an agent that induces cell immortality is an inhibitor of pro-apoptotic polypeptides, e.g., endogenous pro-apoptotic polypeptides, within a stem cell relative to a wild-type stem cell of the same type. In certain embodiments, the pro-apoptotic polypeptide comprises one or more of a Bcl-2 homology domain (e.g., BH1, BH2, BH3 and/or BH4). In specific embodiments, the pro-apoptotic polypeptide comprises BH3, e.g., BIM, PUMA, NOXA, BAK, BAX, BIK, BAD, BID, EGL-1, and/or the like. In specific embodiments, the pro-apoptotic polypeptide is a BH3-only polypeptide, e.g., BIM, PUMA, NOXA, BAD, BID, EGL-1, and/or the like.

Any agent that inhibits the activity or level of pro-apoptotic polypeptide(s) within a stem cell relative to a wild-type stem cell of the same type is suitable as an agent that induces cell immortality. In certain embodiments, an agent that reduces the level of pro-apoptotic polypeptide(s) in the conditionally immortalized stem cell is an agent that interferes with expression of pro-apoptotic polypeptides. In some embodiments, an agent that interferes with the expression of pro-apoptotic polypeptides interferes with expression at the translational level or at the transcriptional level of expression. In certain embodiments, an agent that interferes with expression of a pro-apoptotic polypeptide is an RNAi molecule, (e.g., a molecule that interferes with RNA by cleavage of or binding to mRNA encoding a pro-apoptotic polypeptide, for example, mRNA that encodes a polypeptide comprising the BH3 domain). In some embodiments, an RNAi molecule is generated by any suitable means, including by siRNA, miRNA, dsRNA, and/or shRNA. In certain other embodiments, an agent that interferes with expression of a pro-apoptotic polypeptide is a small molecule, e.g., a small organic molecule.

In some embodiments, an agent that inhibits the activity or level of pro-apoptotic polypeptide(s) within a stem cell relative to a wild-type stem cell of the same type acts directly on the pro-apoptotic polypeptide. For example, in some embodiments, an agent that induces cell immortality comprises an agent that binds to and inhibits the activity of a pro-apoptotic polypeptide, such as an antibody or small molecule that binds to and disrupts the natural function of a pro-apoptotic polypeptide.

In certain embodiments, an agent that induces cell immortality, e.g., a polypeptide or a transgene encoding a polypeptide that induces immortality, is, by way of non-limiting example, n-Myc, c-Myc, l-Myc, v-Myc, mTOR, cyclin D1, cyclin D3, STAT3, STAT5, AML-ETO, AKT, ICN-1, hTERT, PDK-1, MLL-ENL, IL3 receptor β chain, β-catenin, Hedgehog family (Shh, Ihh, Dhh), Bmi-1, c-Jun, Wnt, Bcl-2, Bcl-6, Bcl-10, epidermal growth factor receptor (EGFR, ErbB-1, HER1), ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family; platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family; TRK receptor family; ephrin (EPH) receptor family; AXL receptor family; leukocyte tyrosine kinase (LTK) receptor family; TIE receptor family, angiopoietin 1,2; receptor tyrosine kinase-like orphan receptor (ROR) receptor family; discoidin domain receptor (DDR) family; RET receptor family; KLG receptor family; RYK receptor family; MuSK receptor family; Transforming growth factor β (TGF-β) receptors, TGF-.beta.; Cytokine receptors, Class I (hematopoietin family) and Class II (interferon/IL-10 family) receptors, tumor necrosis factor (TNF) receptor superfamily (TNFRSF), death receptor family; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), .beta.-catenin (CTNNB1), cell division cycle 27 (CDC27), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: β-Dgalactose 2-α-Lfucosyltransferase (LDLR/FUT) fusion protein, HLA-A2. arginine to isoleucine exchange at residue 170 of the .alpha.-helix of the .alpha.2-domain in the HLA-A2 gene (HLA-A*201-R170I), HLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class I, NFYC, OGT, OS-9, pml-RARalpha fusion protein, PRDX5, PTPRK, K-ras (KRAS2), N-ras (NRAS), HRAS, RBAF600, SIRT2, SNRPD1, SYT-SSX1 or -SSX2 fusion protein, Triosephosphate Isomerase, BAGE, BAGE-1, BAGE-2, 3, 4, 5, GAGE-1, 2, 3, 4, 5, 6, 7, 8, GnT-V (aberrant N-acetyl glucosaminyl transferase V, MGAT5), HERV-K-MEL, KK-LC, KM-HN-1, LAGE, LAGE-1, CTL-recognized antigen on melanoma (CAMEL), MAGE-A1 (MAGE-1), MAGE-A2, MAGE-A3, MAGE-A4, MAGE-A5, MAGE-A6, MAGE-A8, MAGE-A9, MAGE-A10, MAGE-A11, MAGE-A12, MAGE-3, MAGE-B1, MAGE-B2, MAGE-B5, MAGE-B6, MAGE-C1, MAGE-C2, mucin 1 (MUC1), MART-1/Melan-A (MLANA), gp100, gp100/Pmell7 (SILV), tyrosinase (TYR), TRP-1, HAGE, NA-88, NY-ESO-1, NY-ESO-1/LAGE-2, SAGE, Sp17, SSX-1,2,3,4, TRP2-INT2, carcinoembryonic antigen (CEA), Kallikrein 4, mammaglobin-A, OA1, prostate specific antigen (PSA), TRP-1/gp75, TRP-2, adipophilin, interferon inducible protein absent in melanoma 2 (AIM-2), BING-4, CPSF, cyclin D1, epithelial cell adhesion molecule (Ep-CAM), EphA3, fibroblast growth factor-5 (FGF-5), glycoprotein 250 (gp250), EGFR (ERBB1), HER-2/neu (ERBB2), interleukin 13 receptor .alpha.2 chain (ILI 3Ralpha2), IL-6 receptor, intestinal carboxyl esterase (iCE), alpha-feto protein (AFP), M-CSF, mdm-2, MUC1, p53 (TP53), PBF, PRAME, PSMA, RAGE-1, RNF43, RU2AS, SOX10, STEAP1, survivin (BIRC5), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA661, LDHC, MORC, SGY-1, SPO11, TPX1, NY-SAR-35, FTHL17, NXF2, TDRD1, TEX15, FATE, TPTE, immunoglobulin idiotypes, Bence-Jones protein, estrogen receptors (ER), androgen receptors (AR), CD40, CD30, CD20, CD19, CD33, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), β-human chorionic gonadotropin, squamous cell carcinoma antigen, neuron-specific enolase, heat shock protein gp96, GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), simian virus 40 (SV40) derived transforming genes and proteins, Human papilloma virus (HPV) proteins (HPV-E6, HPV-E7, major or minor capsid antigens, others), Epstein-Barr virus (EBV) proteins (EBV latent membrane proteins—LMP1, LMP2; others), Hepatitis B or C virus proteins, Human immunodeficiency virus (HIV) proteins, functional homologs, functional analogs, or functional fragments thereof. In certain embodiments, transgenes that encode onco-peptides, other immortalization transgenes, functional homologs, functional analogues, or functional fragments thereof utilized in any method described herein include transgenes that encode a polypeptide that induces cell viability, survival and/or proliferation.

In certain embodiments, a transgene that conditionally over-expresses a polypeptide that induces cell immortality (e.g., an onco-peptide) comprises an element that is responsive to tetracycline or an analogue thereof (e.g., doxycycline). In certain instances, the transgene that encodes any polypeptide described herein (e.g., an onco-peptide) is driven by tTA or rtTA (e.g., TRE-Myc). As such, in certain embodiments, a conditionally immortalized stem cell described herein comprises a first transgene that encodes a polypeptide that induces cell immortality, wherein the first transgene comprises one or more TREs and further comprises a second transgene encoding a polypeptide that conditionally activates the one or more TREs (e.g., tTA or rtTA).

In certain embodiments, a conditionally immortalized stem cell utilized in any method described herein comprises a transgene that expresses a conditionally activated polypeptide that induces cell immortality (e.g., an onco-peptide), wherein the polypeptide expressed by the transgene is a fusion polypeptide. In some embodiments, the fusion polypeptide of a polypeptide comprises a receptor (e.g., an estrogen receptor (ER), wherein modulation (e.g., agonism, antagonism, and/or binding with a ligand) of the receptor activates the survival and proliferative characteristics of the fusion polypeptide. For example, in certain embodiments the conditionally activated polypeptide is a fusion polypeptide of an onco-peptide, such as, by way of non-limiting example, Myc-ER. In some embodiments, a conditionally immortalized stem cell is produced by contacting the conditionally immortalized stem cell with a conditionally activated polypeptide that induces cell immortality (e.g., an onco-peptide), e.g., Myc-ER.

In some instances, an agent that induces immortality, e.g., an onco-peptide or anti-apoptotic polypeptide is optionally expressed or synthesized outside the conditionally immortalized stem cell and subsequently delivered to the conditionally immortalized stem cell to be immortalized or conditionally immortalized. In certain embodiments, an agent that induces cell immortality that is expressed or synthesized outside of the conditionally immortalized stem cell and subsequently delivered to the conditionally immortalized stem cell is produced by contacting the conditionally immortalized stem cell with a transduction domain that enables the polypeptide to be delivered to the conditionally immortalized stem cell. In certain specific embodiments, an agent that induces cell immortality that is expressed or synthesized outside the conditionally immortalized stem cell and subsequently delivered to the conditionally immortalized stem cell is, e.g., Tat-Myc, Vpr-Myc, VP22-Myc, Tat-Bcl-2, Vpr-Bcl-2, VP22-Bcl-2, Tat-Bcl-x, Vpr-Bcl-x, VP22-Bcl-x, Tat-Bcl-XL, Vpr-Bcl-XL, VP22-Bcl-XL, Tat-Mcl-1, Vpr-Mcl-1, VP22-Mcl-1, Tat-CED-9, Vpr-CED-9, VP22-CED-9, Tat-A1, Vpr-A1, VP22-A1, Tat-Bfl-1, Vpr-Bfl-1, VP22-Bfl-1, Tat-Bcl-w, Vpr-Bcl-w, and/or VP22-Bcl-w. In certain embodiments, an onco-peptide comprising a receptor, e.g., ER or GR, also further comprises a transduction domain that enables the polypeptide to be delivered to the conditionally immortalized stem cell, e.g., Tat-Myc, Vpr-Myc, Tat-Myc-ER, Vpr-Myc-ER, VP22-Myc-ER, Tat-Myc-GR, Vpr-Myc-GR, and/or VP22-Myc-GR.

In certain instances, the conditionally immortalized stem cell comprising an agent that induces cell immortality that comprises a transduction domain is prepared by culturing a stem cell with the polypeptide comprising the transduction domain. In specific embodiments, a conditionally immortalized stem cell is prepared by culturing a stem cell with (1) Tat-Myc, Vpr-Myc, Tat-Myc-ER, Vpr-Myc-ER, VP22-Myc-ER, Tat-Myc-GR, Vpr-Myc-GR, or VP22-Myc-GR; and (2) Tat-Bcl-2, Vpr-Bcl-2, VP22-Bcl-2, Tat-Bcl-x, Vpr-Bcl-x, VP22-Bcl-x, Tat-Bcl-XL, Vpr-Bcl-XL, VP22-Bcl-XL, Tat-Mcl-1, Vpr-Mcl-1, VP22-Mcl-1, Tat-CED-9, Vpr-CED-9, VP22-CED-9, Tat-A1, Vpr-A1, VP22-A1, Tat-Bfl-1, Vpr-Bfl-1, VP22-Bfl-1, Tat-Bcl-w, Vpr-Bcl-w, or VP22-Bcl-w. In some embodiments, the polypeptide that comprises a transduction domain and is encoded by a protooncogene is, e.g., Tat-Myc, Vpr-Myc, Tat-Myc-ER, Vpr-Myc-ER, VP22-Myc-ER, Tat-Myc-GR, Vpr-Myc-GR, or VP22-Myc-GR. In certain embodiments, the conditionally immortalized stem cells (e.g., hematopoietic stem cells) are those set forth or prepared by a method set forth in U.S. 2007/0116691, which is hereby incorporated by reference for this disclosure.

In some embodiments, an immortalized or conditionally immortalized stem cell is generated by contacting a stem cell with an agent that induces immortality, (e.g., an onco-peptide or transgene expressing or over-expressing an onco-peptide). In some embodiments, an immortalized or conditionally immortalized stem cell is generated by contacting a stem cell with an agent that induces immortality, (e.g., an onco-peptide or transgene expressing or over-expressing an onco-peptide), in combination with at least one other agent selected from an agent that: induces immortality, (e.g., another onco-peptide, and/or another transgene expressing or over-expressing an onco-peptide), an inhibitor of an endogenous antagonist of an inducer of cell immortality, an anti-apoptotic polypeptide, an inhibitor of pro-apoptotic polypeptides, or a combination thereof.

Immortalized or conditionally immortalized stem cells (e.g., hematopoietic stem cells) utilized in a method described herein are prepared in any suitable manner. In some embodiments, a conditionally immortalized stem cell is produced by contacting the conditionally immortalized stem cell with a polypeptide and/or a transgene (e.g., an oncogene or protooncogene) encoding a polypeptide that induces immortality. In certain embodiments, the conditionally immortalized stem cell is produced by contacting the conditionally immortalized stem cell with an onco-peptide (e.g., Myc) and/or a transgene encoding an onco-peptide (e.g., Myc). In some embodiments wherein the immortalized or conditionally immortalized stem cells (e.g., hematopoietic stem cells) utilized in method described herein comprise a transgene that encodes an onco-peptide, any method described herein optionally further comprises excising the transgene from the nucleus of either the immortalized or conditionally immortalized stem cell prior to differentiation, or from the nucleus of the cell of a selected type following differentiation.

In certain embodiments, stem cells (e.g., hematopoietic stem cells) utilized in method disclosed herein comprise an onco-peptide or transgene expressing an onco-peptide in combination with at least one other agent that induces cell immortality. Specific examples of such combinations include an onco-peptide or transgene expressing an onco-peptide (e.g., Myc, Myc-ER, Tat-Myc, Vpr-Myc, Tat-Myc-ER, Vpr-Myc-ER, VP22-Myc-ER, Myc-GR, Tat-Myc-GR, Vpr-Myc-GR, VP22-Myc-GR, cyclin D1, cyclin D3, and/or HIF-1a) with an inhibitor of an endogenous antagonist of an agent that induces cell immortality (e.g., an inhibitor of a cyclin-dependent kinase inhibitor (e.g., p16, p19, p21, or p27) and/or an inhibitor of a transcriptional repressor that suppresses expression of a gene that induces cell immortality (e.g., a member of the MAD family of transcriptional repressors (e.g., MAD-1)).

In other embodiments, combinations of agents that induce immortality include an onco-peptide or transgene expressing an onco-peptide (e.g., Myc, Myc-ER, Tat-Myc, Vpr-Myc, Tat-Myc-ER, Vpr-Myc-ER, VP22-Myc-ER, Myc-GR, Tat-Myc-GR, Vpr-Myc-GR, VP22-Myc-GR, cyclin D1, cyclin D3, and/or HIF-1a) with an anti-apoptotic polypeptide comprising one or more of a Bcl-2 homology domain (e.g., Bcl-2, Bcl-x, Bcl-XL, Mcl-1, CED-9, A1, Bfl-1, Bcl-w or the like); and/or an inhibitor of a pro-apoptotic polypeptide (e.g., BIM, PUMA, NOXA, BAK, BAX, BIK, BAD, BID, EGL-1). In certain embodiments, specific combinations of agents that induce immortality in stem cells (e.g., hematopoietic stem cells) utilized in method disclosed herein are: a Myc polypeptide and a Bcl-2 polypeptide; a Myc polypeptide and an inhibitor of a pro-apoptotic polypeptide, e.g., BIM. In certain embodiments, the inhibitor comprises nucleic acids, amino acids, or is a small organic molecule.

In some other embodiments, stem cells (e.g., hematopoietic stem cells) utilized in method disclosed herein comprise a combination of an inhibitor of an endogenous antagonist of an inducer of stem cell immortalization with at least one other agent that induces stem cell immortalization, e.g., another inhibitor of an endogenous antagonist of an inducer of stem cell immortalization, and/or an onco-peptide, and/or an anti-apoptotic polypeptide, and/or an inhibitor of pro-apoptotic polypeptides. Specific non-limiting examples of such combinations include an inhibitor of MAD-1 with a Bcl-2 polypeptide, and an inhibitor of MAD-1 with an inhibitor of a pro-apoptotic polypeptide, e.g., BIM.

Also included in certain embodiments are combinations of agents that induce cell immortality, wherein at least one of the agents, up to and including all of the agents, is conditionally expressed or activated. For example, such combinations include, by way of non-limiting example, conditionally activated onco-peptides, e.g., Myc-ER, Tat-Myc, Vpr-Myc, Tat-Myc-ER, Vpr-Myc-ER, VP22-Myc-ER, Myc-GR, Tat-Myc-GR, Vpr-Myc-GR and/or VP22-Myc-GR, in combination with anti-apoptotic polypeptides, e.g., Bcl-2, Tat-Bcl-2, Vpr-Bcl-2, VP22-Bcl-2, Tat-Bcl-x, Vpr-Bcl-x, VP22-Bcl-x, Tat-Bcl-XL, Vpr-Bcl-XL, VP22-Bcl-XL, Tat-Mcl-1, Vpr-Mcl-1, VP22-Mcl-1, Tat-CED-9, Vpr-CED-9, VP22-CED-9, Tat-A1, Vpr-A1, VP22-A1, Tat-Bfl-1, Vpr-Bfl-1, VP22-Bfl-1, Tat-Bcl-w, Vpr-Bcl-w, or VP22-Bcl-w.

Transgenes and polypeptides described herein are delivered to a plurality of stem cells (e.g., hematopoietic stem cells) to be immortalized or conditionally immortalized in any suitable manner such as, by way of non-limiting example, transfecting into a stem cell using a vector, microinjection, transfection, transduction, electroporation, or like methods. In certain instances, transgenes are constructed into a vector by any suitable techniques including, e.g., using polymerase chain reaction to isolate a gene or a fragment of a gene or genes from a genome, using restriction enzymes for the modification of a gene, or a fragment of a gene or genes isolated from a genome, using nucleic acid modifying enzymes such as topoisomerases, DNA ligases, DNA nucleases, and using methods related to obtaining mRNA from a cell and converting mRNA to cDNA and cloning the cDNA into a suitable vector for further cloning.

In certain embodiments, protein transduction is used to introduce the immortalization agent(s) into the cells. For example, for protein transduction, the fusion proteins have been purified prior to transduction. As a result, genetic modification of the cell is not necessary in order to conditionally immortalize the cell.

In certain embodiments, viral transduction is used. In some embodiments, the gene for immortalization, such as Myc or Bcl-2, is cloned into a viral vector in which the gene expression is derived under the control of various viral inducers, such as herpes simplex virus thymidine kinase inducer or HIV LTR (long term repeat) inducer. In specific embodiments, the plurality of stem cells (e.g., hematopoietic stem cells) is contacted with a viral vector comprising a nucleic acid sequence encoding a Myc gene, a Bcl-2 gene, or a combination thereof. In some embodiments, the plurality of stem cells (e.g., hematopoietic stem cells) is contacted with a retroviral vector comprising a nucleic acid sequence encoding a Myc gene, a Bcl-2 gene, or a combination thereof. In some embodiments, the plurality of stem cells (e.g., hematopoietic stem cells) is contacted with an adenoviral vector comprising a nucleic acid sequence encoding a Myc gene, a Bcl-2 gene, or a combination thereof. In some embodiments, the plurality of stem cells (e.g., hematopoietic stem cells) is contacted with a lentiviral vector comprising a nucleic acid sequence encoding a Myc gene, a Bcl-2 gene, or a combination thereof. In some embodiments, cell transfection methods are used for the delivery of transgene(s). Thus, in some embodiments, genes are cloned into a mammalian expression vectors and the vector containing the transgene is delivered by commercially available cell transfection agents based, e.g., on cationic lipid technologies. In some embodiments, an electroporation method, which is a variation of transfection methodologies, is optionally used to deliver mammalian expression vectors. In certain instances, for efficient transfection, the vector is linearized before the transfection.

In some embodiments, any of the method described herein utilizing an immortalized or stem cell comprising a transgene that encodes a polypeptide that induce immortality (e.g., an onco-peptide) further comprise excising the transgene from the stem cell prior to differentiation or from the differentiated cell following differentiation. In certain embodiments, excision of the transgene is achieved via the use of a Cre-loxP or similar system. In this system, the transgene that encodes the polypeptide that induces cell survival, cell viability and/or cell proliferation comprises a sequence element, e.g., a loxP locus (5'-ATAACTTCGTATA ATGTATGC TATACGAAGT-TAT-3' (SEQ ID NO: 1)), inserted before and after the transgene. In certain instances, the loxP sequence is recognized by a recombinase (e.g., Cre), which is optionally utilized to excise a transgene located between two loxPs (e.g., a sequence element that encodes the polypeptide that induces cell survival, cell viability and/or cell proliferation). In one embodiment using Cre-loxP system, a viral plasmid is constructed in which fusion transgene (e.g., Tat-Myc, Vpr-Myc, Tat-Myc-ER, or Tat-MYC) is flanked by two loxP sequences. In certain embodiments, the transgene is integrated into the genomes of a plurality of stem cells (e.g., hematopoietic stem cells) by any suitable method (e.g., transduction).

Differentiation

In some embodiments, provided herein is a method for preparing a plurality of cells of a selected type, comprising:
(a). providing a stem cell;
(b). introducing a transgene encoding an agent that induces immortality or an onco-peptide that induces immortality into the conditionally immortalized stem cell to produce a conditionally immortalized stem cell; and
(c). inducing differentiation of the plurality of immortalized a plurality of stem cells (e.g., hematopoietic stem cells) to a plurality of cells of the type.

In certain embodiments, an immortalized stem cell utilized in any method described herein is a conditionally immortalized stem cell (ctlt-stem cell). In some embodiments, differentiation of a conditionally immortalized stem cell occurs under conditions wherein immortalization of the conditionally immortalized stem cell is not induced. In other embodiments, differentiation of a conditionally immortalized stem cell occurs under conditions wherein immortalization of the conditionally immortalized stem cell is induced.

In some embodiments, a method disclosed herein further comprises contacting the conditionally immortalized stem cell with a polypeptide that induces differentiation and/or a transgene encoding a polypeptide that induces differentiation. In some embodiments, the polypeptide comprises an export sequence and plasma membrane retention element. In certain embodiments, when the polypeptide in the cell or expressed by the cell is retained on the plasma membrane, the polypeptide further comprises a sequence that facilitates the removal of the polypeptide from the cell surface. In certain embodiments, the sequence that facilitates the removal of the polypeptide from the cell surface is a protease cleavage site. In some embodiments, the protease cleavage site is the substrate of a serum protease.

In certain embodiments, the polypeptide that induces differentiation is a cytokine. In certain embodiments, the cytokine is a growth and/or differentiation factor. In certain embodiments, the growth and/or differentiation factor is EPO, THPO or G-CSF.

A cell produced by a method described herein is any cell that is differentiable from a normal or wild type stem cell. For example, provided herein are method for preparing an erythrocyte (erythrocyte), a lymphoid cell, a B lymphocyte, a T lymphocyte, a natural killer cell, a neutrophil, a basophil, an eosinophil, a monocyte, a macrophage, a thrombocyte, or the like from an immortalized or conditionally immortalized stem cell. In specific embodiments, an erythrocyte is prepared from an immortalized or conditionally immortalized stem cell. In other specific embodiments, a thrombocyte is prepared from an immortalized or conditionally immortalized stem cell. In some embodiments, a differentiated cell prepared according to any method described herein is an anucleated cell, e.g., an erythrocyte.

Furthermore, selected types of cells prepared by differentiating immortalized or conditionally immortalized stem cells according to any method described herein include, by way of non-limiting example, lymphoid progenitor cells, lymphoblasts, prolymphocyte, naive T cells, T helper cells, natural killer Cells, cytotoxic T cells, memory T cells, regulatory T cells, γδ T cells, progenitor B cells, early pro-B cells, last pro-B cells, large pre-B cells, small pre-B cells, immature B cells, mature B cells, plasma B cells, memory B cells, B-1 cells, lymphoid dendritic cells, common myeloid progenitor cells, megakaryoblasts, promegakayroblasts, megakaryocytes, thrombocytes, proerythroblasts, basophilic erythroblasts, polychromatic erythroblasts, orthochromatic erythroblasts, reticulocytes, erythrocytes, myeloblasts, basophilic promyelocytes, basophilic myelocytes, basophilic metamyelocytes, basophilic band cells, basophils, neutrophilic promyelocytes, neutrophilic myelocytes, neutrophilic metamyelocytes, neutrophilic band cells, neutrophils, eosinophilic promyelocytes, eosinophilic myelocytes, eosinophilic metamyelocytes, eosinophilic band cells, eosinophils, monoblasts, promonocytes, monocytes, macrophages, myeloid dendritic cells, and mast cells. Moreover, in some embodiments, immortalized or conditionally immortalized stem cells differentiate into cells of non-lineages, such as cells of epithelia, liver, lung, gastrointestinal tract, brain, heart, skeletal muscle, and skin.

In some embodiments, a bone cell (osteocyte), cartilage cell (chondrocyte, fat cell (adipocyte), lung cell, or the like are prepared from an immortalized or conditionally immortalized mesenchymal stem cell. In certain embodiments, a neuron, astrocyte, oligodendrocyte, or the like is prepared from an immortalized or conditionally immortalized neural stem cell. In some embodiments, epithelial cells (e.g., a component cell of the epithelium of a tissue) are prepared from an immortalized or conditionally immortalized epithelial stem cell. In certain embodiments, keratinocyte or the like are prepared from an immortalized or conditionally immortalized skin stem cell. In some embodiments, a hair follicular cell, an epidermal cell or the like are prepared from an immortalized or conditionally immortalized follicular stem cell.

In certain embodiments, an immortalized or conditionally immortalized stem cell is differentiated to a selected type of cell in any suitable manner. In some embodiments, an immortalized or conditionally immortalized stem cell is differentiated by contacting the cell with an agent that induces differentiation, e.g., a cytokine. In certain embodiments, contacting the immortalized or conditionally immortalized stem cell with an agent that induces differentiation of the immortalized or conditionally immortalized stem cell comprises culturing the agent (or combination of agents) with the immortalized or conditionally immortalized stem cell. In certain instances, cytokines are recognized by a variety of cellular receptors on cell surface and trigger cellular responses functionally associated with the receptor. In one aspect, utilized herein cytokine refers to any classes of cytokine, including, an autocrine cytokines, a paracrine cytokines or an endocrine cytokines. Agents utilized to induce differentiation (e.g., a cytokine) or combinations of agents are optionally utilized. In specific embodiments, agents (e.g., cytokines) utilized in differentiating immortalized or conditionally immortalized stem cells (e.g., hematopoietic stem cells) include, by way of non-limiting example, one or more of an interleukin (IL) family ranging from IL-1 through IL-35, an interferon (IFN), a leukocyte migration inhibitory factor (LMIF), a leukemia inhibitory factor (LIF), onconstatin M (OSM), osteopontin, erythropoietin (EPO), thrombopoietin (THPO), transforming growth factor beta (TGFβ), a tumor necrosis factors (TNF), stem cell factor (SCF), granulocyte colony stimulating factor (G-CSF), granulocyte macrophage colony stimulating factor (G-CSF), macrophage colony stimulating factor (M-CSF), beta-thromboglobuin, a C family chemokine, a CC family chemokine, a CXC family chemokine, a CX3C family chemokine, thrombocyte factor 4, a macrophage inflammatory protein, a tumor autocrine motility factor, a hepatocyte growth factor, a neuroleukin, a T-cell suppressor factor, a B-cell activating factor, an ectodysplasins, a Fas-ligand protein, OX40 ligand, RANK ligand, a lymphotoxin, or a combination thereof.

For example, in some embodiments, inducing differentiation of an immortalized or conditionally immortalized stem cell to an erythrocyte or an erythrocyte progenitor according to any method described herein includes contacting (e.g., culturing) the immortalized or conditionally immortalized stem cell with EPO. In further embodiments, inducing differentiation of an immortalized or conditionally immortalized stem cell to an erythrocyte or an erythrocyte progenitor according to any method described herein includes contacting (e.g., culturing) the immortalized or conditionally immortalized stem cell with IL-3, IL-6, G-CSF, and EPO. Furthermore, in certain embodiments, inducing differentiation of an immortalized or conditionally immortalized stem cell to a thrombocyte according to any method described herein includes contacting (e.g., culturing) the immortalized or conditionally immortalized stem cell with THPO. In further embodiments, inducing differentiation of an immortalized or conditionally immortalized stem cell to a thrombocyte progenitor according to any method described herein includes contacting (e.g., culturing) the immortalized or conditionally immortalized stem cell with IL-3, IL-6, G-CSF, and THPO. In some embodiments, cytokines, such as dexamethasone, β-estradiol, insulin growth factor-1, and/or cyclosporin A, are utilized in differentiation method described herein.

In some instances, prior to contacting the plurality of stem cells (e.g., hematopoietic stem cells) with an agent that induces differentiation, an agent that induces immortalization, e.g., an onco-peptide and/or transgene encoding an onco-peptide and/or anti-apoptotic peptide, is excised from the conditionally immortalized stem cell. Excision of the agent that induces immortalization is achieved in any suitable manner, including via bacterial recombinases (e.g., Cre or Flp).

In specific embodiments, provided herein is a method for producing a plurality of differentiated cells, comprising:
(d). providing a stem cell;
(e). introducing a transgene encoding an agent that induces immortality or a polypeptide that induces immortality into the conditionally immortalized stem cell to produce an immortalized or conditionally immortalized stem cell; and
(f). inducing differentiation of the immortalized stem cell to the selected type of cell.

In various embodiments, the conditionally immortalized stem cell is, by way of non-limiting example, a stem cell, a mesenchymal stem cell, a neural stem cell, a epithelial stem cell, a intestinal stem cell, a cardiac myocyte progenitor stem cell, a skin stem cell, a follicular stem cell, a skeletal muscle stem cell, an osteoblastic precursor stem cell, a liver stem cell, an embryonic stem cell or the like. In specific embodiments, the plurality of stem cells (e.g., hematopoietic stem cells) is obtained from any suitable source. For example, in some embodiments, a stem cell is obtained from the bone marrow, peripheral blood, umbilical cord, or fetal tissue of an individual or is procured from a source that obtained a stem cell from the bone marrow, peripheral blood, umbilical cord, or fetal tissue of an individual. In some embodiments, the plurality of stem cells (e.g., hematopoietic stem cells) are obtained by anesthetizing the stem cell donor, puncturing the posterior superior iliac crest with a needle, and performing aspiration of bone marrow cells with a syringe. In some embodiments, the plurality of stem cells (e.g., hematopoietic stem cells) is harvested from circulating blood. In some embodiments, the plurality of stem cells (e.g., hematopoietic stem cells) in the bone marrow are coaxed to migrate from marrow to circulating blood in greater numbers by injecting the stem cell donor with a cytokine, such as granulocyte-colony stimulating factor (G-CSF). In certain embodiments, the plurality of stem cells (e.g., hematopoietic stem cells) is harvested from a human umbilical cord or placenta. In some embodiments, the source of the plurality of stem cells (e.g., hematopoietic stem cells) is the developing blood-producing tissues of fetal animals. In humans, stem cells (e.g., hematopoietic stem cells) are found in the circulating blood of a human fetus by about 12 to 18 weeks.

Furthermore, in some embodiments, provided herein are method of preparing progenitors or precursors of any of the cells described herein. For example, in some embodiments, any method described herein is utilized to prepare a progenitor or a precursor of an erythrocyte or a thrombocyte. Such progenitors or precursors include, by way of non-limiting example, a myeloid progenitor cell. Progenitor cells are cells with restricted differentiation potential. They are produced from a plurality of stem cells (e.g., hematopoietic stem cells) and give rise to a subset of terminally differentiated, specialized cells. For example, myeloid progenitor cells give rise to myeloid lineage cells and lymphoid progenitor cells give rise to lymphoid progenitor cells, such as T cell or B cells. In certain embodiments, progenitor cells are produced according to any method described herein.

In certain embodiments, cells prepared by any of the method described herein are further separated to achieve homogeneity of the final cell product. Erythrocytes, for example, go through diverse stages of different morphology and characters during differentiation method. In certain embodiments, in order to collect a plurality of erythrocytes that are substantially homologous, various methods are employed to separate erythrocytes according to their shape, size, weight, and/or volume. Various separation methods include, by way of non-limiting example, centrifugation, use of sorting machines, or filtering. In certain embodiments, when terminally differentiated products are not readily distinguishable from non-differentiated cells in the culture, the terminally differentiated products are separated by the presence of marker(s) specifically associated with the terminally differentiated form of cell. For example, in some embodiments, in order to isolate terminally differentiated macrophages, a culture containing a mixture of macrophages, immortalized or conditionally immortalized stem cells and other progenitor cells are treated with fluorescent-conjugated Gr-1 antibodies to identify macrophages in the culture. In some embodiments, the identified macrophages are isolated to a homogeneous population by the use of FACS equipment.

Figure 5:
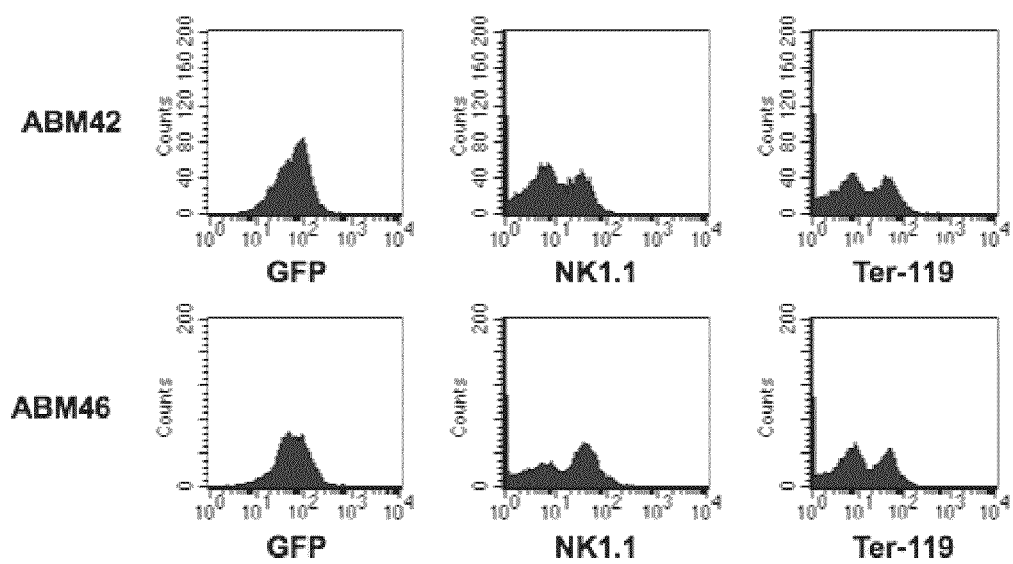
FIG. 5 illustrates the differentiation of ctlt-hematopoietic stem cells into Ter-119 expressing erythroid progenitors in vitro.

In certain embodiments, progenitor cells that are not terminally differentiated are produced by any of the method described herein. For example, in some embodiments, subjects in need of a sustained blood supply rather than instant infusion of a large quantity of erythrocytes is delivered reticulocytes or proerythroblasts prepared according to a method described herein for sustained in vivo production of erythrocytes. In certain embodiments, in order to facilitate differentiation from immortalized or conditionally immortalized stem cells to progenitor cells rather than terminally differentiated cells, cytokine selection, concentration, and/or the time of removal from the culture medium are optionally adjusted. By adjusting these parameters, for example, erythrocyte differentiation is directed toward a condition favoring the production of proerythroblasts rather than to the terminally differentiated erythrocytes. In certain embodiments, progenitor cells are identified and/or isolated in any suitable manner. In certain embodiments, isolation identification and/or separation are achieved by, by way of non-limiting example, the use of FACS equipment. In some embodiments, erythrocyte progenitors are identified and/or isolated based on their ability to attach to Ter-119 antibody. FIG. 5 illustrates differentiation of conditionally immortalized a plurality of stem cells (e.g., hematopoietic stem cells) into Ter-119 expressing erythroid progenitors in vitro.

Erythrocytes and Thrombocytes

Furthermore, provided herein are differentiated cells (e.g., erythrocytes, thrombocytes or progenitors thereof) prepared according to any method described herein.

In some embodiments, provided herein is a method for preparing an erythrocyte, comprising:
  (g). providing a conditionally immortalized stem cell; and
  (h). inducing differentiation of the conditionally immortalized stem cell into an erythrocyte or an erythrocyte progenitor.

In specific embodiments, inducing differentiation of a conditionally immortalized stem cell into an erythrocyte or a progenitor thereof comprises contacting the conditionally immortalized stem cell with erythropoietin (EPO).

In some embodiments, inducing differentiation of an immortalized or conditionally immortalized stem cell to an erythrocyte or an erythrocyte progenitor according to any method described herein includes contacting (e.g., culturing) the immortalized or conditionally immortalized stem cell with EPO. In further embodiments, inducing differentiation of an immortalized or conditionally immortalized stem cell to an erythrocyte or an erythrocyte progenitor according to any method described herein includes contacting (e.g., culturing) the immortalized or conditionally immortalized stem cell with G-CSF, and EPO. In some embodiments, inducing differentiation of an immortalized or conditionally immortalized stem cell to an erythrocyte or an erythrocyte progenitor according to any method described herein includes contacting (e.g., culturing) the immortalized or conditionally immortalized stem cell with IL-3, G-CSF, and EPO. In certain embodiments, inducing differentiation of an immortalized or conditionally immortalized stem cell to an erythrocyte or an erythrocyte progenitor according to any method described herein includes contacting (e.g., culturing) the immortalized or conditionally immortalized stem cell with IL-3, G-CSF, IL-6, and EPO. In further embodiments, inducing differentiation of an immortalized or conditionally immortalized stem cell to an erythrocyte or an erythrocyte progenitor according to any method described herein includes contacting (e.g., culturing) the immortalized or conditionally immortalized stem cell with IL-3, G-CSF, cyclosporine A, and EPO. In further embodiments, inducing differentiation of an immortalized or conditionally immortalized stem cell to an erythrocyte or an erythrocyte progenitor according to any method described herein includes contacting (e.g., culturing) the immortalized or conditionally immortalized stem cell with G-CSF and EPO and one or more of IL-3, IL-6, cyclosporine A, or TNF-α.

In some embodiments, provided herein is a method for preparing a thrombocyte, comprising:
  (i). providing a conditionally immortalized stem cell; and
  (inducing differentiation of the conditionally immortalized stem cell into a thrombocyte or a thrombocyte progenitor.

In specific embodiments, inducing differentiation of a conditionally immortalized stem cell into an erythrocyte or a progenitor thereof comprises contacting the conditionally immortalized stem cell with thrombopoietin (THPO).

II. Screening Method

In certain embodiments, provided herein are method and kits for identifying compounds that selectively induce differentiation of conditionally immortalized stem cells (e.g., hematopoietic stem cells) by:
  (a). providing a conditionally immortalized stem cell;
  (b). contacting the conditionally immortalized stem cell with a compound;
  (c). detecting or measuring the effect of the compound on the state of differentiation of the conditionally immortalized stem cell; and
  (d). optionally isolating and characterizing the compound that was contacted with the immortalized stem cell in the case that the identity of the compound is unknown when contacted with the immortalized stem cell.

Any of the immortalized or conditionally immortalized stem cells disclosed herein is used in a method of screening for compounds that induce differentiation of the conditionally immortalized stem cells (e.g., hematopoietic stem cells) into cells of a selected type.

In certain embodiments, contacting the conditionally immortalized stem cell with a compound comprises contacting the conditionally immortalized stem cell with a compound under conditions wherein the conditionally immortalized stem cell is not in the immortalized state (i.e., external factors or molecules that are used to conditionally induce the immortalized state have been removed from or have not been exposed to the conditionally immortalized stem cells (e.g., hematopoietic stem cells)). For example, in some embodiments wherein the conditionally immortalized stem cell is produced by contacting the conditionally immortalized stem cell with a Myc-ER or Myc-GR polypeptide, the conditionally immortalized stem cell is contacted with the compound in the absence of an estrogen receptor modulator or ligand (e.g., tamoxifen or 4-hydroxytamoxifen) or the glucocorticoid receptor ligand (e.g., mifepristone). Thus, in these specific embodiments, the ER or GR is not activated and the Myc domain of the fusion polypeptide remains non-functional. In some embodiments, the conditionally immortalized cell comprises TRE-Myc, e.g., Myc activated by tTA or rtTA, and the conditionally immortalized stem cell is contacted with the compound while the TRE-Myc is inactivated, e.g., in the absence of tetracycline in the case of tTA activated Myc and in the presence of doxycycline in the case of rtTA activated Myc.

In some instances, prior to contacting a plurality of stem cells (e.g., hematopoietic stem cells) with a compound in the screening method, an agent that induces immortalization, e.g., onco-peptide and/or transgene encoding an onco-peptide and/or anti-apoptotic peptide, is excised from the conditionally immortalized stem cell. Excision of the agent that induces immortalization is achieved in any suitable manner, including via bacterial recombinases (e.g., Cre or Flp).

In certain embodiments, the screen for identifying compounds that induce differentiation is done in the absence of EPO. In such cases, the compounds identified by the screen induce differentiation of the conditionally immortalized stem cells (e.g., hematopoietic stem cells) to cells of selected type, e.g., erythrocytes, without the assistance of EPO. In some embodiments, when the screen is conducted in the absence of EPO, expression of the EPO receptor is disrupted. Compounds identified by the screening method disclosed herein that induce differentiation of a plurality of stem cells (e.g., hematopoietic stem cells) to erythrocytes in the absence of EPO is administered therapeutically without the risk of developing erythroleukemia from chronic administration of EPO.

In other embodiments, the screen for compounds that induce differentiation of a plurality of stem cells (e.g., hematopoietic stem cells) is conducted in the presence of EPO. When EPO is present, compounds identified by the screening method modulate (e.g., increase or decrease) the activity of EPO. Compounds that modulate the activity of EPO identified by the screening method disclosed herein are effective for the treatment of erythroid leukemias.

In certain embodiments, the screen for identifying compounds that induce differentiation is done in the absence of THPO. In such cases, the compounds identified in the screen induce differentiation of the conditionally immortalized stem cells (e.g., hematopoietic stem cells) to cells of selected type, e.g., thrombocytes, without the assistance of THPO. In some embodiments, when the screen is conducted in the absence of THPO, expression of the THPO receptor is disrupted. In other embodiments, the screen is conducted in the presence of THPO. When THPO is present, compounds identified by the screening method modulate (e.g., increase or decrease) the activity of THPO.

In certain embodiments, detection or measurement of the effect of the compound on the state of differentiation of the conditionally immortalized stem cell is achieved by any suitable method, including, by way of non-limiting example, gain-of-function screens, gene-expression and microarray analysis, immunocytochemistry, labeled-antibody detection or measurement of cellular markers, HPLC analysis of cellular molecular signatures, small-molecule fluorophore screens, and cellular functional analysis.

In certain embodiments, the compounds contacted with the cells are isolated by suitable methods known by those of ordinary skill in the art, e.g., by way of non-limiting example, gas chromatography, high performance liquid chromatography, flash chromatography, precipitation, and crystallization. In certain embodiments, the compound characterized is characterized using suitable methods known in the art, e.g., by way of non-limiting example, NMR, IR, mass spectrometry, and X-ray crystallography.

In some embodiments, provided herein is a compound identified by any method described herein. The compound is identified by screening individual compounds or mixtures compounds. The conditionally immortalized stem cells (e.g., hematopoietic stem cells) are optionally contacted with individual compounds or collections of compounds, e.g., combinatorial libraries of compounds. Compounds are screened in a high-throughput manner, using calorimetric analysis to identify compounds that induce differentiation or modulate the activity of other differentiating agents.

In certain embodiments, kits for identifying compounds suitable for inducing differentiation of a plurality of stem cells (e.g., hematopoietic stem cells), particularly conditionally immortalized stem cells (e.g., hematopoietic stem cells), comprise a plurality of a plurality of stem cells (e.g., hematopoietic stem cells), particularly conditionally immortalized stem cells (e.g., hematopoietic stem cells), wherein the kit describes the screening method for identifying compounds that induce differentiation of a plurality of stem cells (e.g., hematopoietic stem cells) set forth herein.

III. Methods of Treatment

Cells prepared according to any method herein are optionally used therapeutically or as sources of cells for research purposes.

Enucleated Cell Deficiency Disorders

Disclosed herein, in certain embodiments, is a method of treating a disorder characterized by a deficiency of anucleated cells, comprising: administering an anucleated cell prepared according to a method disclosed herein. In some embodiments, the disorder is an anemia (e.g., aplastic anemia, pernicious anemia, iron deficiency anemia, sickle cell anemia, spherocytosis, hemolytic anemia), Gaucher's disease, hemolysis, neutropenia, thrombocytopenia, granulocytopenia, hemophilia, Hodgkin's lymphoma, Non-Hodgkin's lymphoma, B cell chronic lymphoma, Burkitt's lymphoma, Follicular-like lymphoma, diffused large B-cell lymphoma, multiple myeloma, acute myeloid leukemia, pre-B acute lymophcytic leukemia, pre-T acute lymphocytic leukemia, acute promeylocytic leukemia, refractory leukemia, or combinations thereof. In certain instances, the disorder characterized by a deficiency in anucleated cells results from (partially or fully) chemotherapy. In some embodiments, an anucleated cell produced by a method disclosed herein is co-administered with chemotherapy.

In some embodiments, thrombocytes, erythrocytes or progenitors thereof are administered to or transfused into an individual in need thereof, e.g., suffering from a loss of blood. In some embodiments, a patient suffering from a low number of a subset of myeloid cells is treated by giving myeloid precursor cells to compensate for myeloid deficiency. In certain embodiments, wherein an immediate transfusion is needed, large quantities of erythrocytes and/or thrombocytes prepared according to method described herein are administered to an individual. In some embodiments, sustained transfusion of blood and/or thrombocytes is desired and progenitors of erythrocytes and/or thrombocytes are administered to the individual.

Cells of a selected type prepared according to any method described herein are optionally utilized in cell replacement therapy and/or in a supplementary therapy to subject with various conditions including, by way of non-limiting example, anemia, neutropenia, thromocytopenia, granulocytopenia, Hodgkin's lymphoma, Non-Hodgkin's lymphoma, B cell chronic lymphoma, Burkitt's lymphoma, Follicular-like lymphoma, diffused large B-cell lymphoma, multiple myeloma, acute myeloid leukemia, pre-B acute lymophcytic leukemia, pre-T acute lymphocytic leukemia, acute promeylocytic leukemia, refractory leukemia, or combinations thereof.

Delivery Devices

Cells prepared according to any method disclosed herein are optionally administered to patients as delivery vehicles for polypeptides of interest, e.g., for therapeutic or diagnostic purposes. For example, key advantages of using cells prepared by the method described herein, e.g., erythrocytes and thrombocytes, for protein delivery include the transient nature of the cells, the lack of genetic material in the fully mature, anucleated cells, and the tolerance of the "self vessel" for delivery by the lymphoid compartment from ontogeny.

In some embodiments, the polypeptide is a therapeutically beneficial polypeptide. In other embodiments, the polypeptide is a diagnostic polypeptide. In certain embodiments, a polypeptide is not an onco-peptide. In some embodiments, a polypeptide comprises an export sequence and plasma membrane retention element, such that the polypeptide in the cell or expressed by the cell is retained on the plasma membrane. In some non-limiting embodiments, the plasma membrane retention element is a GPI-linked protein, CD8, or CD16. In certain embodiments, when the polypeptide in the cell or expressed by the cell is retained on the plasma membrane, the polypeptide further comprises a sequence that facilitates the removal of the polypeptide from the cell surface, such as a protease cleavage site. In some embodiments, the protease cleavage site is the substrate of a serum protease, for example, a human serum protease. Cells produced in this manner are used to deliver specific peptides to a patient by introducing them into the peripheral blood of a patient, where serum proteases will cleave and release the peptide from the cell surface. Cells expressing selected polypeptides on the plasma membrane, including cleavable polypeptides that are produced in the manner disclosed herein are vehicles for delivery of therapeutic proteins. For example, in certain embodiments, when erythrocytes are used as vehicles for protein delivery, key advantages include the transient nature of the erythrocytes and encoded proteins that they deliver, the lack of genetic material contained in the fully mature, anucleated erythrocytes, the use of a vessel for protein delivery that is tolerated by the lymphoid compartment from ontogeny, and ability to generate the cells for delivery in vitro.

In some embodiments, the polypeptide is a decoy receptor. In certain embodiments, the decoy receptor is a cytokine receptor. In some embodiments, the cytokine receptor is soluble. In certain embodiments, the decoy receptor is IL3R-Fc, IL6R-Fc, TNF-αR-FC, IFN-αR-Fc, or BAFFR-Fc.

In other embodiments, a polypeptide is a toxin. In certain embodiments, the toxin is ricin or diphtheria toxin.

In some embodiments, a polypeptide is an angiogenesis inhibitor.

In other embodiments, a polypeptide is a proangiogenic factor.

In still other embodiments, a polypeptide is a lymphangiogenic factor.

In further embodiments, a polypeptide is a vasodilatory peptide.

In other embodiments, a polypeptide is an antigen.

In still other embodiments, a polypeptide is a protease. In certain embodiments, the protease is specific for fibrotic tissues in embolitic masses.

In some embodiments, a polypeptide is a receptor for a microbe, e.g., a virus, a bacterium, a fungus, a protozoon, or a parasite. In some specific embodiments, the microbe receptor is a genetically modified microbial receptor that out-competes endogenous receptors for the microbe due to a higher binding affinity for the microbe.

In some embodiments, a cell produced by a method disclosed herein is a delivery vehicle for a polypeptide angiogenesis inhibitor. In other embodiments, a polypeptide is a proangiogenic factor and/or lymphangiogenic factor, and such cells produced by a method disclosed herein is administered to patients to deliver the polypeptides for the treatment of, for example, frost bite, cancer-related vasoconstriction, or rheumatic arthritis.

In still other embodiments, a polypeptide in a cell or expressed by a cell produced by any of the method disclosed herein is a vasodilatory peptide. In this manner, cells produced by the method disclosed herein are vehicles for delivering the proteins for the treatment of vascular constriction during cardiac infarction, child delivery, or migraine headaches.

In other embodiments, a polypeptide is an antigen. Cells produced by the method disclosed herein that express an antigen are vehicles for delivery of thetigens to produce an immune response.

In some embodiments, such cells are delivered to patients in conjunction with toll-like receptor ligands (TLR ligands) in order to boost life-long immunity.

In still other embodiments, a polypeptide is a protease. In certain embodiments, the protease is specific for fibrotic tissues in embolitic masses. In certain embodiments, for example, cells produced by the method disclosed herein that express proteases specific for fibrotic tissues in embolitic masses are administered to patients to alleviate blood clot formation or to reduce the risk of pulmonary embolisms.

In some embodiments, a polypeptide is a receptor for a virus. In some embodiments, cells expressing viral receptors produced by the method disclosed herein are administered to patients to, for example, decrease viral load by sequestering viruses from their natural target cells.

Figure 6:
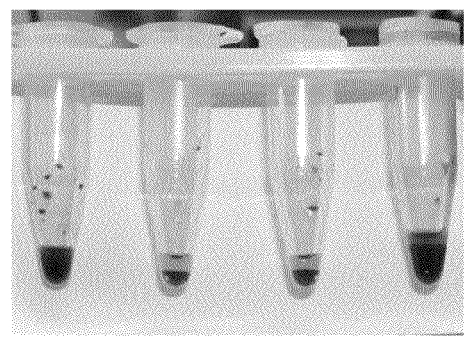
FIG. 6 illustrates a view of the reconstitution of erythrocytes in vivo after lethal irradiation by transplant of ctlt-hematopoietic stem cells.
Figure 7:
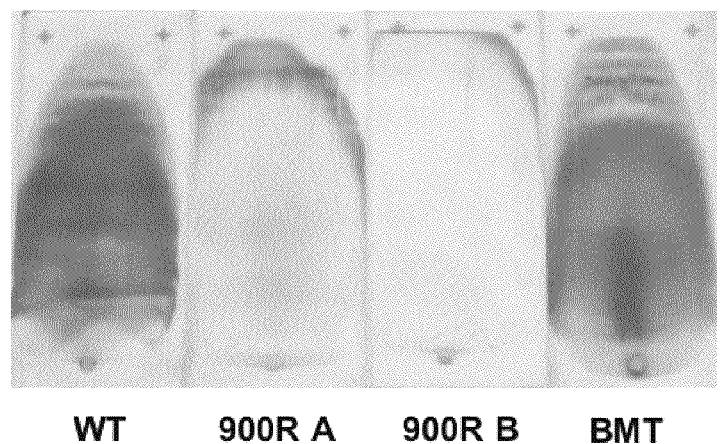
FIG. 7 illustrates a view of the reconstitution of erythrocytes in vivo after lethal irradiation by transplant of ctlt-hematopoietic stem cells
Figure 8:
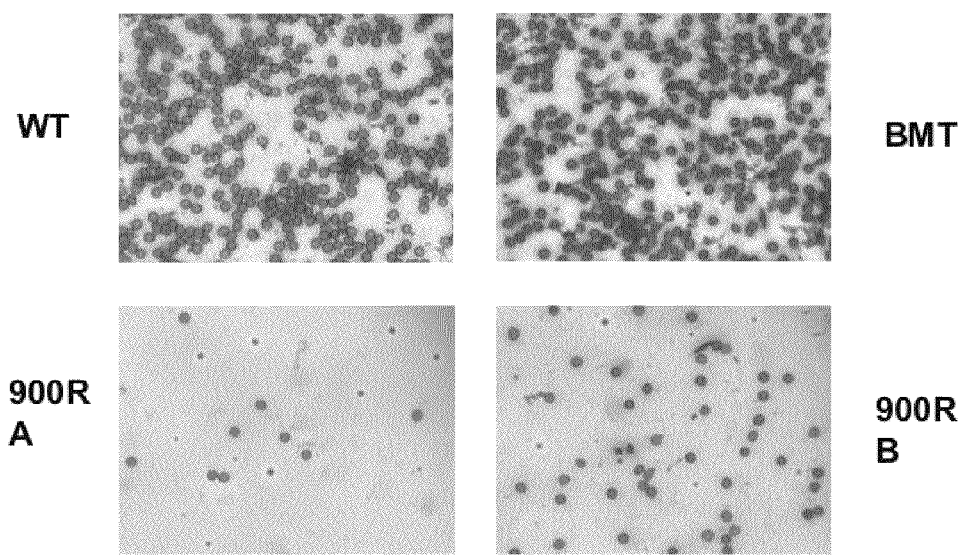
FIG. 8 illustrates a view of the reconstitution of erythrocytes in vivo after lethal irradiation by transplant of ctlt-hematopoietic stem cells.

FIG. 6 illustrates reconstitution of erythrocytes in vivo after lethal irradiation by transplant of conditionally immortalized stem cells (e.g., hematopoietic stem cells)—macroscopic view I. FIG. 7 illustrates reconstitution of erythrocytes in vivo after lethal irradiation by transplant of conditionally immortalized stem cells (e.g., hematopoietic stem cells)—macroscopic view II. FIG. 8 illustrates reconstitution of erythrocytes in vivo after lethal irradiation by transplant of conditionally immortalized stem cells (e.g., hematopoietic stem cells)—microscopic view of anucleated erythrocytes.

IV. Bioreactors

In some embodiments, production of differentiated blood cells (e.g., erythrocytes or thrombocytes) is achieved by the use of bioreactors. In certain embodiments, the bioreactors are flow reactors or batch reactors. In specific embodiments, flow reactors are continuous flow reactors or batch-flow reactors. In certain embodiments, synthesis in a reactor is achieved by seeding a vessel with an immortalized or conditionally immortalized stem cell population. In some embodiments, the immortalized or conditionally immortalized stem cell population is induced or allowed to proliferate (e.g., due to promotion of cellular survival, viability and/or proliferation caused by a polypeptide therein). Once a sufficient population (e.g., at least 0.1 kg, 1 kg, 10 kg, or 100 kg) of immortalized or conditionally immortalized stem cells are prepared, the conditionally immortalized stem cells (e.g., hematopoietic stem cells) are contacted with a culture medium that induces differentiation of the conditionally immortalized stem cells (e.g., hematopoietic stem cells) to the desired cells, e.g., according to any method described herein. In certain embodiments, the differentiated cells (e.g., progenitors and/or terminally differentiated cells) desired are then collected.

Immortalized or conditionally immortalized stem cells described herein are capable of being cryopreserved (e.g., for less than about 1 day, about 1 day, about 2 days, about 3 days, about 4 days, about 5 days, about 6 days, about 7 days, about 2 weeks, about 3 weeks, about 1 month, about 3 months, about 4 months, about 6 months, about 8 months, about 9 months, about 12 months). This feature allows for convenient on-demand synthesis of a selected type of cells on a large scale. In certain embodiments, immortalized or conditionally immortalized stem cells are processed to remove the immortalization genes and are then cryopreserved for future differentiation. In some embodiment, immortalized or conditionally immortalized stem cells are differentiated into a progenitor, for example a megakaryoblast, and cryopreserved for immediate production of thrombocytes.

Provided in certain embodiments herein is a reactor system, comprising:
(k). feeder vessel comprising a plurality of conditionally immortalized stem cells (e.g., hematopoietic stem cells);
(l). a reaction vessel comprising a plurality of conditionally immortalized stem cells (e.g., hematopoietic stem cells) and an agent for inducing differentiation of the conditionally immortalized stem cells (e.g., hematopoietic stem cells) into erythrocytes or thrombocytes, wherein the reaction vessel is in communication with the feeder vessel; and
(m). a downstream harvest vessel in communication with the reaction vessel, the harvest vessel comprising a plurality of the erythrocytes or thrombocytes.

In certain embodiments, the feeder vessel further comprises an agent for inducing proliferation of the conditionally immortalized stem cells (e.g., hematopoietic stem cells). In some embodiments, the system further comprises a reactor management system that regulates the communication between the reaction vessel and the feeder vessel, and between the reaction vessel and the downstream harvest reactor. In certain embodiments, the conditionally immortalized stem cell is produced by contacting the conditionally immortalized stem cell with a Myc gene or polypeptide and optionally a Bcl-2 gene (i.e., a Bcl-2 transgene) or polypeptide. In some embodiments, the conditionally immortalized stem cell is produced by contacting the conditionally immortalized stem cell with a Myc-ER fusion gene or fusion polypeptide and optionally a Bcl-2 gene or polypeptide. In certain embodiments, the agent for inducing proliferation of a plurality of stem cells (e.g., hematopoietic stem cells) is an estrogen receptor modulator. In some embodiments, the agent for inducing differentiation of the conditionally immortalized stem cells (e.g., hematopoietic stem cells) to erythrocytes is IL-3 and EPO. In certain embodiments, the agent for inducing differentiation of the conditionally immortalized stem cells (e.g., hematopoietic stem cells) to thrombocytes is IL-3 and THPO.

EXAMPLES

Example 1

FIG. 1A illustrates a schematic representation of retroviral constructs used to transduce primary murine HSC cells with MYC.ER and Bcl-2. Variants of the pMSCV backbone are generated to encode the cDNAs for human MYC.ER or Bcl-2 as well as an IRES element and a reporter gene (EGFP). The resulting viruses generate bicistronic transcripts such that the level of reporter gene expression correlates with the level of expression of the first cDNA. FIG. 1B illustrates Flow cytometric analyses of HSCs obtained 5-fluorouracil treated donors following transduction with pMIG-MYC.ER and pMIG-Bcl-2. FIG. 1C illustrates kinetics of leukemogenesis in mice transplanted with the transduced HSCs shown in panel B. Cohorts of lethally irradiated mice are transplanted with $10^5$ HSCs that have been transduced with pMIG-MYC.ER and pMIG-Bcl-2. One week after transplantation, the mice are given weekly injections of 4OHT. The curve represents the percentage of surviving mice at a given point in time after the 4OHT injections began (day 0 in the graph). All of the mice died uniformly of an AML-like leukemia. The data shown here are from one experiment representative of 4 independent experiments. FIG. 1D illustrates FACS analysis of a ctlt-hematopoietic stem cell soon after recovery from the bone marrow of leukemic mice. At an early stage of the method of establishing a conditionally immortalized hematopoietic stem cell line, the cells uniformly express high levels of GFP, predominantly express high levels of c-kit and Sca-1, and do not express Flk-2, CD34 or lineage markers such as CD19, B220 (shown in the figure), or Thy1.2, Mac-1, Gr-1, Ter-119. FIG. 1E illustrates FACS analysis of a conditionally immortalized hematopoietic stem cell line that has been established. Once the conditionally immortalized hematopoietic stem cell line is expanded and cryopreserved, it retains a stable surface phenotype that is represented in panel B. These cells express high levels of Sca-1, but have reduced surface levels of c-Kit, and remain negative for Flk-2, CD34, B220, CD19 or the other lineage markers (thy1.2, Gr-1, Mac-1, Ter-119; not shown). The reduction of c-kit levels from the surface appears to be a result of continuous signaling, since they require G-CSF to retain their HSC-like phenotype. FIG. 1F illustrates FACS analysis of stem cell marker in normal, unmanipulated Hematopoietic stem cells from the bone marrow of wild type C57/BL6 mice. Bone marrow stem cells are obtained from wild type, unmanipulated C57/BL6 mice. The cells are stained with antibodies to c-kit, sca-1, Flk-2, and CD34, in order to compare the expression levels of the marker proteins by normal HSCs and in the ctlt-hematopoietic stem cell lines.

Example 2

Figure 2:
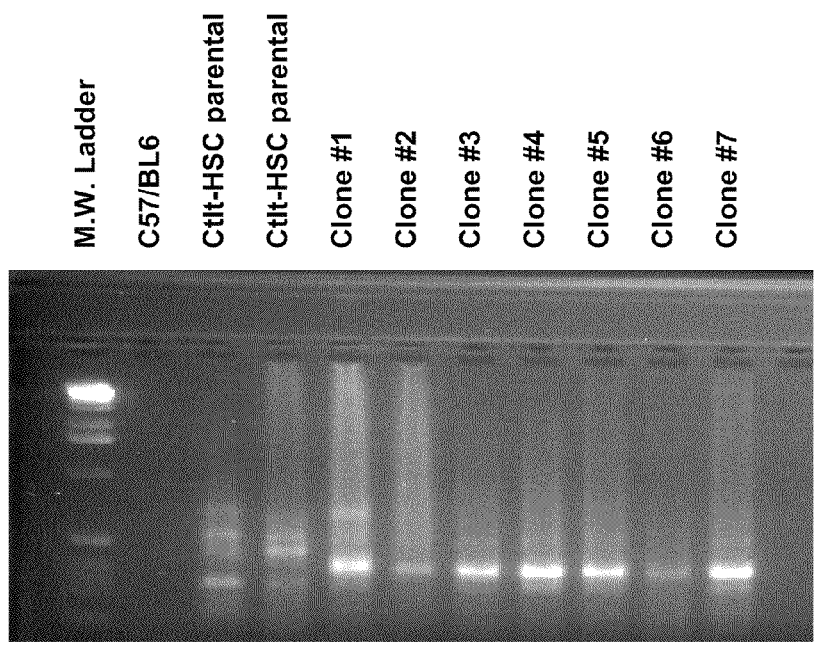
FIG. 2 illustrates Analysis of clonality of ctlt-hematopoietic stem cell lines by PCR amplification of retroviral insertions.

FIG. 2 illustrates analysis of clonality of conditionally immortalized hematopoietic stem cell lines by PCR amplification of retroviral insertions. We isolate genomic DNA from normal bone marrow cells obtained from C57/BL6 mice, or from two parental cell lines, or seven cell lines derived from single cell clones of the parental cell lines. The integrated retroviral insertions are amplified with a nested two-stage PCR procedure. Lane 1 shows the pattern of normal C57/BL6 cells. Lanes 2 and 3 show the pattern of retroviral integrations in multiclonal cell lines. Lanes 4-10 show the pattern of retroviral insertions in cell lines originally derived from single cell clones of either parental cell line. Like the parental lines, clonal populations are able to rescue mice from lethal irradiation and give rise to hematopoietic lineages.

Example 3

Figure 3:
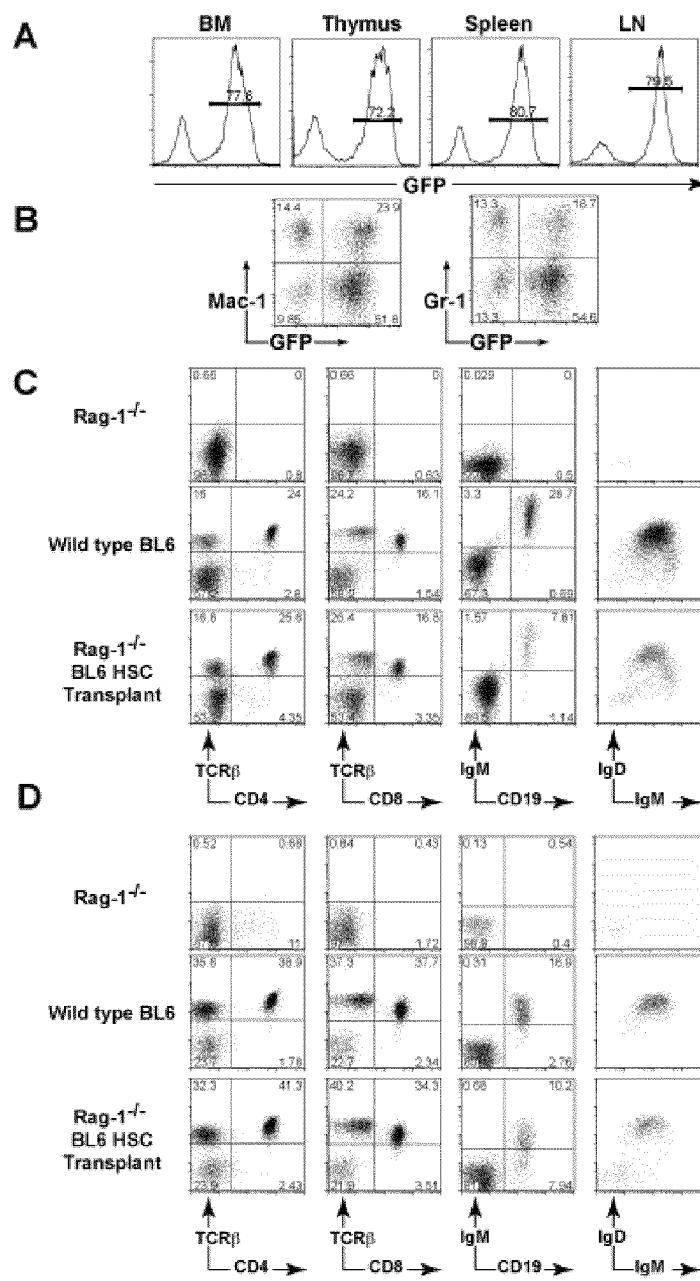
FIG. 3 illustrates characteristics of mature immune cells that arise following transplantation of ctlt-hematopoietic stem cells.

FIG. 3 illustrates the characterization of mature immune cells that arise following transplantation of ctlt-hematopoietic stem cells. FIG. 3A illustrates frequency of cells derived from ctlt-hematopoietic stem cells in lymphoid tissues after transplantation. Cohorts of C57/BL6 mice are lethally irradiated and given transplants consisting of $10^3$ ctlt-hematopoietic stem cells and $3 \times 10^5$ carrier whole bone marrow cells derived from Rag-1$^{-/-}$ mice. The cells that develop from conditionally immortalized hematopoietic stem cells are traced in vivo by virtue of the retrovirally encoded reporter gene, GFP. The frequency of hematopoietic cells that express GFP in the bone marrow, thymus, spleen and lymph node of chimaeric mice are represented in panel A. These histograms are derived from the organs in one mouse exemplary of each within a cohort of five. FIG. 3B illustrates detection of GFP+ myeloid lineage cells in the bone marrow. We stained bone marrow cells for Mac-1 and Gr-1. Panel B shows that while not all of the myeloid cells found in the bone marrow of chimaeric mice express the retrovirally encoded reporter gene, a significant portion is GFP+ and hence are derived from the ctlt-hematopoietic stem cells. FIG. 3C illustrates analysis of peripheral, mature lymphocytes in the spleen. Spleens from chimaeric mice were analyzed by flow cytometry for mature T and B cells. Panel C shows the presence of TCRαβ T cells that are either CD4 or CD8 single positive. In addition, panel C also shows the detection of CD19+ B cells that express IgM and IgD on their surface. While the frequency of mature T-cells in the spleen is comparable to what is found in wild type, unmanipulated C57/BL6 mice, the development of B-cells is delayed. FIG. 3D illustrates analysis of peripheral, mature lymphocytes in transplant recipient mice following the second serial passage of conditionally immortalized hematopoietic stem cells. Spleens are collected from chimaeric mice, and single cell suspensions are prepared and used for FACS analysis. The frequency of mature T and B cells found in recipients and wild type C57/BL6 mice, are compared. Panel D shows the presence of mature CD4 or CD8 single positive TCRαβ T cells in the spleens at a frequency similar to normal mice. CD19+ IgM+ and IgD+ B cells are present, albeit at a lower frequency than in normal mice.

Example 4

Figure 4:
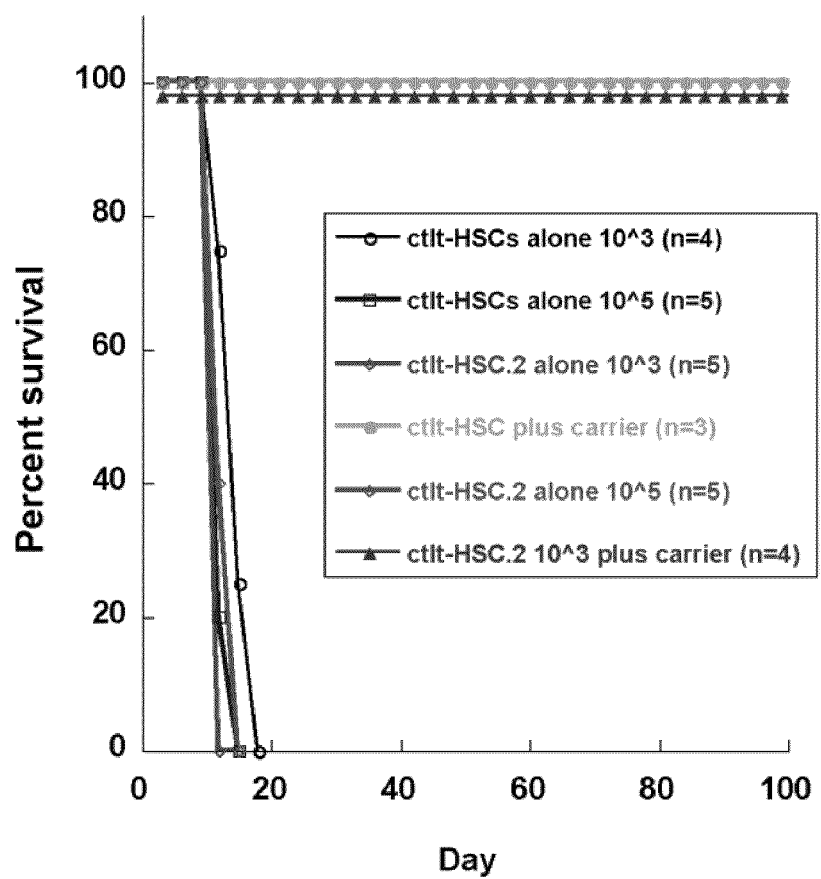
FIG. 4 illustrates long-term rescue from lethal irradiation by ctlt-hematopoietic stem cells.

FIG. 4 illustrates long-term rescue from lethal irradiation by ctlt-hematopoietic stem cells. Transplantation of conditionally immortalized hematopoietic stem cells alone does not confer radioprotection past the cris induced by loss of erythrocytes. Kaplan/Mayer survival curves for cohorts of mice that are lethally irradiated and given transplants consisting of $10^3$ or $10^5$ cells from two different conditionally immortalized hematopoietic stem cell lines (conditionally immortalized hematopoietic stem cell or conditionally immortalized hematopoietic stem cell.2). All of the cohorts consisted of 10 mice and these animals uniformly died of severe anemia. We also represent the mortality curves of two cohorts of mice that are lethally irradiated and given $3 \times 10^5$ carrier whole bone marrow cells derived from Rag-1$^{31/-}$ mice along with $10^3$ conditionally immortalized hematopoietic stem cells from either cell line. The cohorts consisted of 3-4 mice each and the animals remained alive and healthy for up to 6 months after transplantation.

Example 5

In Vivo Treatment of Anemia by Administration of Erythrocytes Produced by a Method Disclosed Herein Two cohorts of healthy mice are given a sublethal dose of irradiation to induce anemia. The first group of anemic mice are administered erythrocytes (produced as disclosed herein) in a suitable carrier. The second group of mice (the control mice) are administered only the suitable carrier. The mortality rate of the two groups of mice is compared to determine the efficacy of administration of erythrocytes disclosed herein to rescue the mice from anemia.

Example 6

In Vivo Treatment of Anemia in a Renal Failure Mouse Model

Anemia is induced in a renal failure mouse model, as reported in the literature. Hamamori, et al. *J. Clin. Invest.* (1995), 95: 1808-1813. Briefly, a two-step nephrectomy is performed on 7-8 week old male nude mice. Anemia in the mice is confirmed by measuring hematocrit levels. The mortality rate of mice receiving administration of erythrocytes produced by a method disclosed herein is compared to the mortality rate of mice receiving the carrier for the cells alone in order to determine the efficacy of administration of erythrocytes disclosed herein for the treatment of anemia resulting from renal failure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein is employed in practicing the invention. It is intended that the following claims define the scope of the invention and that methods and structures within the scope of these claims and their equivalents be covered thereby.

What is claimed is:

1. A method of preparing a plurality of anucleated cells comprising: culturing conditionally immortalized hematopoietic stem cells in the presence of an agent for inducing differentiation to erythrocytes; wherein the agent consists of IL-3 and EPO, and wherein the agent induces the differentiation of conditionally immortalized hematopoietic stem cells to mature erythrocytes thereby producing a plurality of anucleated cells;

wherein the conditionally immortalized hematopoietic stem cells were generated by:
   a. providing a plurality of hematopoietic stem cells with an exogenous MYC molecule; and
   b. providing the hematopoietic stem cells with an exogenous Bcl-2 molecule, an exogenous Bcl-X molecule, or a combination thereof;
      and wherein the activity of the exogenous MYC molecule was suppressed before differentiation.

2. The method of claim 1, wherein the exogenous MYC molecule is c-Myc, l-Myc, n-Myc, s-Myc, or a combination thereof.

3. The method of claim 1, wherein the exogenous MYC molecule is c-Myc.

4. The method of claim 1, wherein the generation of the conditionally immortalized hematopoietic stem cells further comprised culturing the stem cells with IL-3, IL-6, stem cell factor, thrombopoietin, Flt3 ligand, or a combination thereof.

5. The method of claim 1, wherein the exogenous MYC molecule is provided by transfecting the hematopoietic stem cells with a first vector comprising:
   a nucleic acid sequence encoding a MYC molecule;
   wherein the exogenous Bcl-2 molecule, the exogenous Bcl-X molecule, or combination thereof is provided by transfecting the stem cells with a second vector comprising: a nucleic acid sequence encoding a Bcl-2 molecule, a Bcl-X molecule, or a combination thereof.

6. The method of claim 5, wherein the first vector further comprises the hormone-binding domain of the human estrogen receptor.

7. The method of claim 6, further comprising contacting the plurality of hematopoietic stem cells with: estradiol (E2), 4-hydroxytamoxifen (4-OHT), or both.

8. The method of claim 7, wherein the activity of the exogenous MYC molecule was suppressed by no longer contacting the plurality of hematopoietic stem cells with: estradiol (E2), 4-hydroxytamoxifen (4-OHT), or both.

9. The method of claim 5, further comprising inducing translocation of the exogenous MYC molecule to a nucleus.

10. The method of claim 5, wherein the first vector, the second vector, or both the first vector and the second vector is Murine Stem Cell Virus (MSCV), or a derivative thereof.

11. The method of claim 5, wherein the first vector, the second vector, or both the first vector and the second vector is MSCV-(IRES)-GFP, or a derivative thereof.

12. The method of claim 5, wherein the first vector, the second vector, or both the first vector and the second vector is MSCV-(IRES)-GFP, and further comprises woodchuck hepatitis B virus RNA regulatory element (WRE).

13. The method of claim 5, wherein the first vector further comprises the hormone-binding domain of the human glucocorticoid receptor.

14. The method of claim 13, further comprising contacting the plurality of hematopoietic stem cells with mifepristone.

15. The method of claim 13, wherein the activity of the exogenous MYC molecule was suppressed by no longer contacting the plurality of hematopoietic stem cells with mifepristone.

* * * * *